United States Patent [19]

Thompson

[11] 4,267,038
[45] May 12, 1981

[54] CONTROLLED NATURAL PURIFICATION SYSTEM FOR ADVANCED WASTEWATER TREATMENT AND PROTEIN CONVERSION AND RECOVERY

[76] Inventor: Worthington J. Thompson, 109 Powell St., Snow Hill, Md. 21863

[21] Appl. No.: 95,969

[22] Filed: Nov. 20, 1979

[51] Int. Cl.$^3$ .............................. C02F 3/30; C02F 3/32
[52] U.S. Cl. ........................................ 210/602; 47/1.4; 210/151; 210/170; 210/199; 210/202; 210/220; 210/255; 210/260; 210/262; 210/903; 210/758; 210/765; 210/605; 210/630
[58] Field of Search .......................... 47/1.4; 210/2–16, 210/60, 63 R, 151, 170, 195.1, 196, 197, 199, 202, 220, 221 R, 255, 260, 262, DIG. 28

[56] References Cited

U.S. PATENT DOCUMENTS

| | | | |
|---|---|---|---|
| 2,732,663 | 1/1956 | Dewey | 47/1.4 |
| 3,168,465 | 2/1965 | Kraus et al. | 210/DIG. 28 |
| 3,362,104 | 1/1968 | Oswald et al. | 47/1.4 X |
| 3,385,786 | 5/1968 | Klock | 210/12 |
| 3,431,200 | 3/1969 | Davis et al. | 47/1.4 X |
| 3,468,057 | 9/1969 | Buisson et al. | 47/1.4 X |
| 3,521,400 | 7/1970 | Ort | 47/1.4 |
| 3,698,881 | 10/1972 | White | 210/2 X |
| 3,768,200 | 10/1973 | Klock | 47/1.4 |
| 3,900,394 | 8/1975 | Rongved | 210/DIG. 28 |
| 3,955,317 | 5/1976 | Gudin | 47/1.4 X |
| 3,973,043 | 8/1976 | Lynn | 47/1.4 X |
| 3,977,965 | 8/1976 | Tholander et al. | 210/DIG. 28 |
| 3,986,297 | 10/1976 | Ichimura et al. | 47/1.4 |

FOREIGN PATENT DOCUMENTS 43-28933 12/1968 Japan ........................................... 47/1.4

OTHER PUBLICATIONS

"Oversize Ponds Oxidize Wastes", Engineering News-Record, Dec. 5, 1957, pp. 76 and 78.

Primary Examiner—Robert H. Spitzer
Attorney, Agent, or Firm—Walter G. Finch

[57] ABSTRACT

The invention is an improved controlled natural purification system for an advanced wastewater treatment and protein conversion and recovery. The system provides for treating municipal wastewater and associated organic industrial discharges anaerobically and aerobically. The system consists of such treatments in a tank complex where the waste organics are reduced to inorganic forms available for microalgae culture in tanks uniquely designed for rapid growth. The system includes a recovery mechanism to recover the algae for food purposes. Utilizing organic wastewater as the renewable resource, the system has the potential to develop from a wastewater treatment process that removes excess nutrients, producing reusable water and a commercially valuable algal by-product, to large scale algae farming cost-effectively producing millions of tons per year of sterile, stable, high protein algal foodstuff.

17 Claims, 43 Drawing Figures

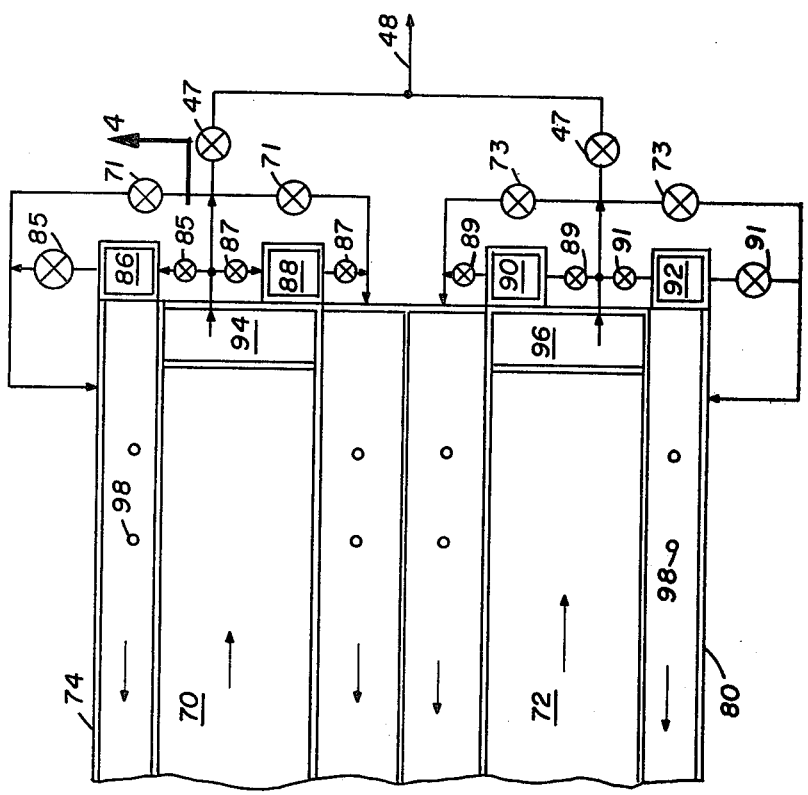
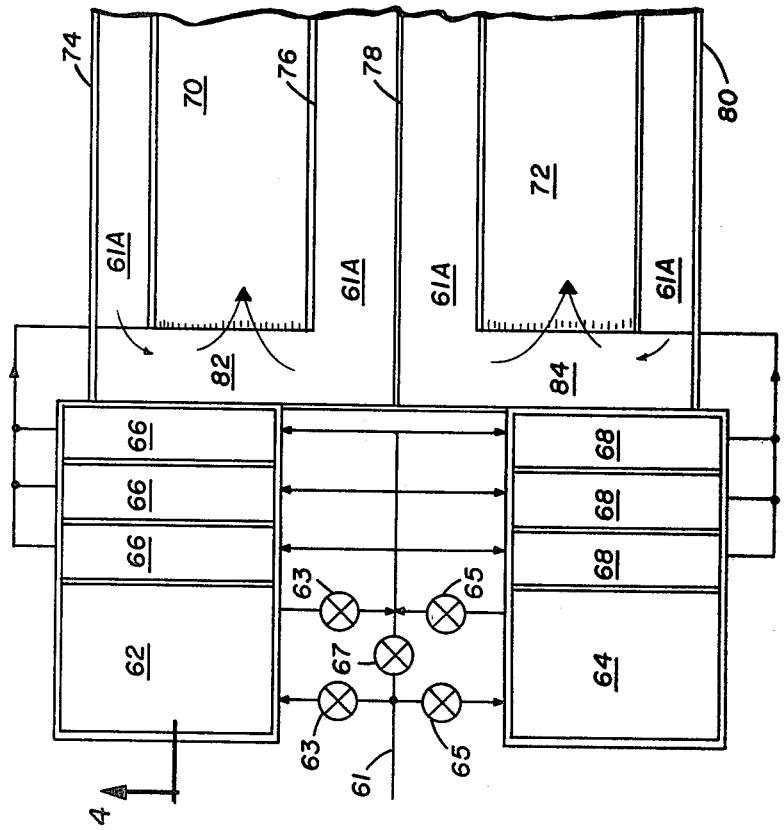
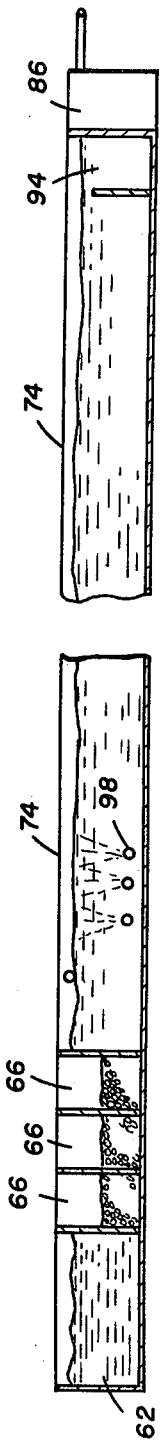
FIG. 3
FIG. 4

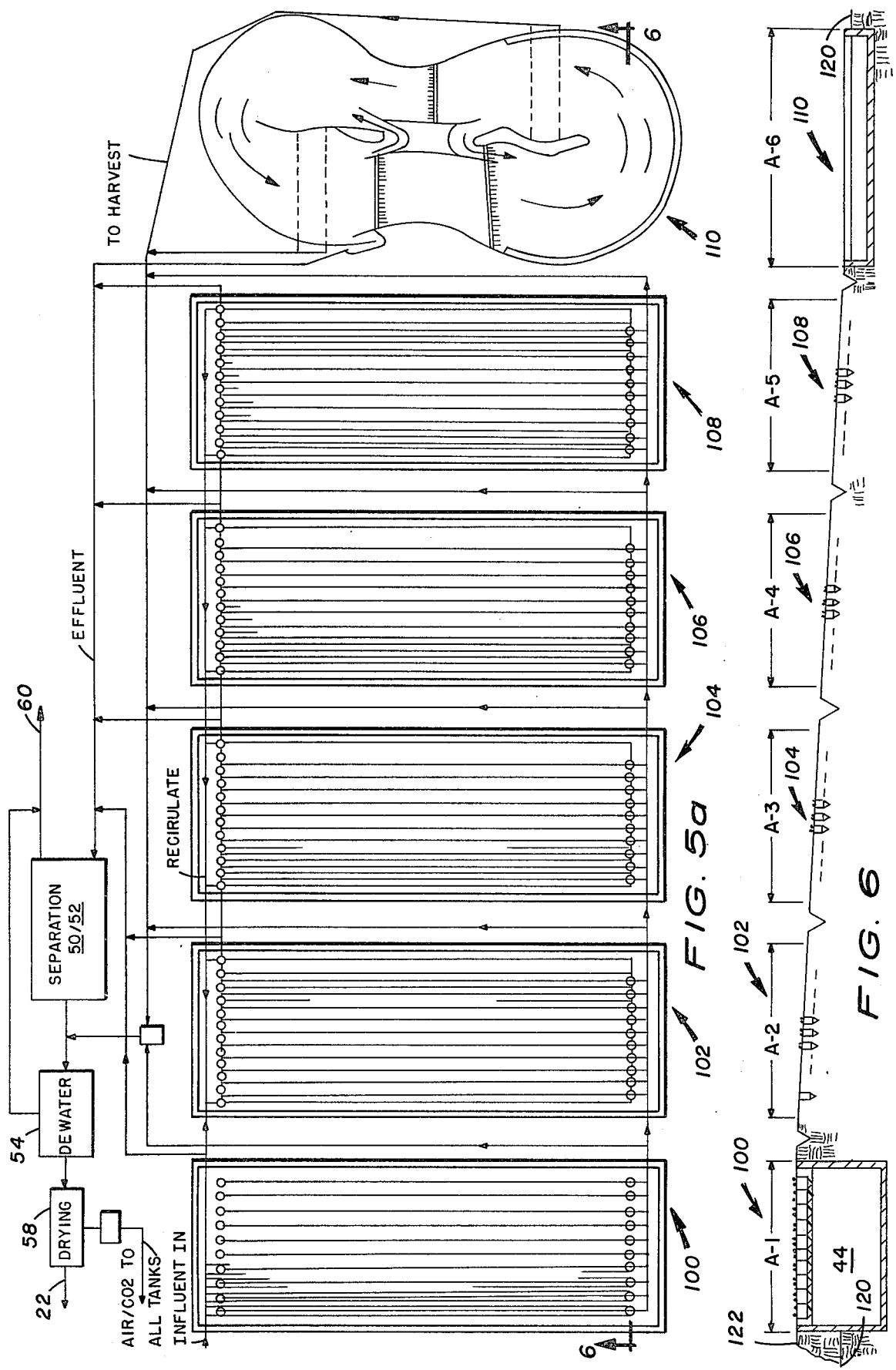

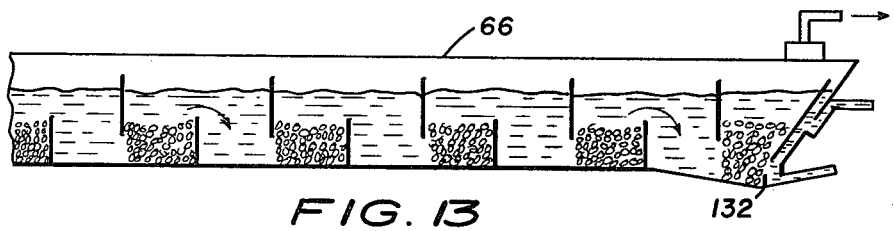
FIG. 13
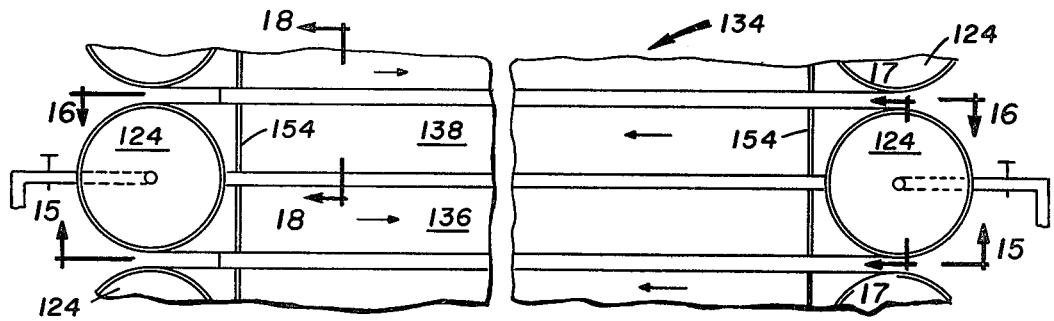
FIG. 14
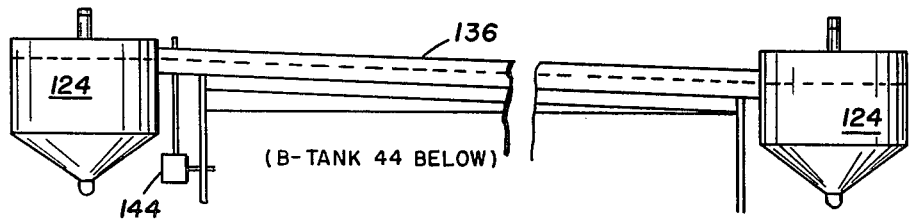
FIG. 15
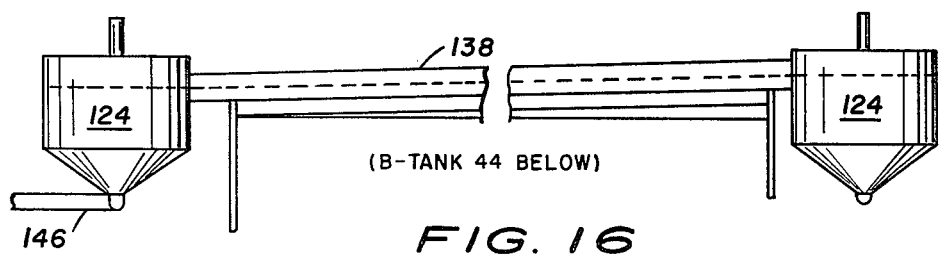
FIG. 16
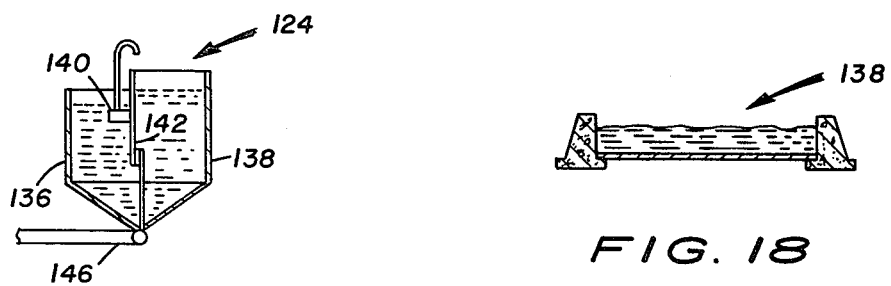
FIG. 17
FIG. 18

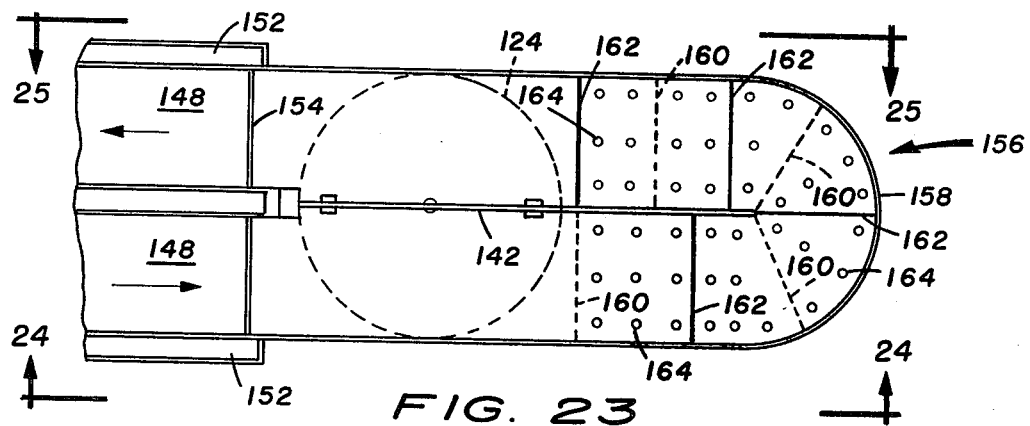
FIG. 23
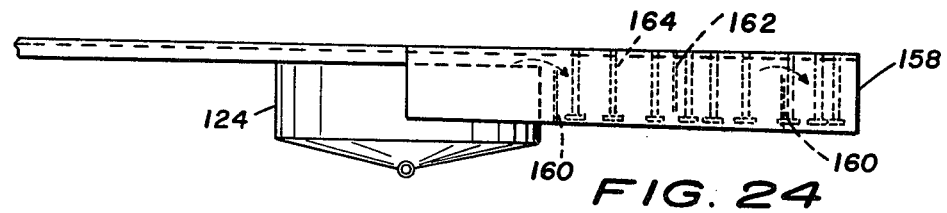
FIG. 24
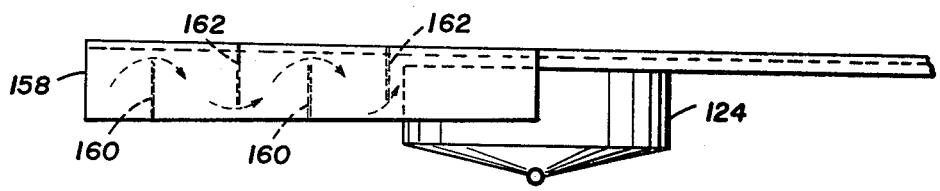
FIG. 25
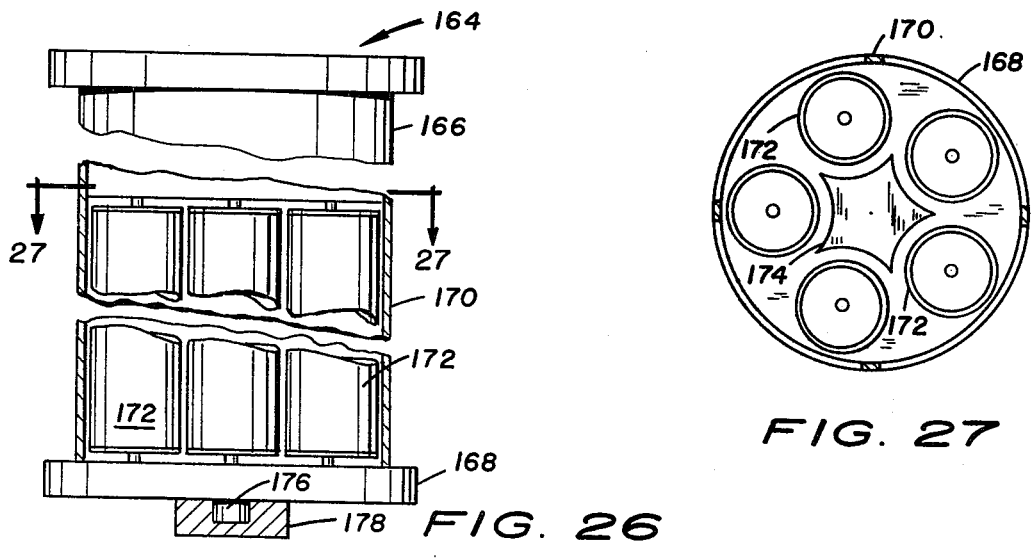
FIG. 27
FIG. 26

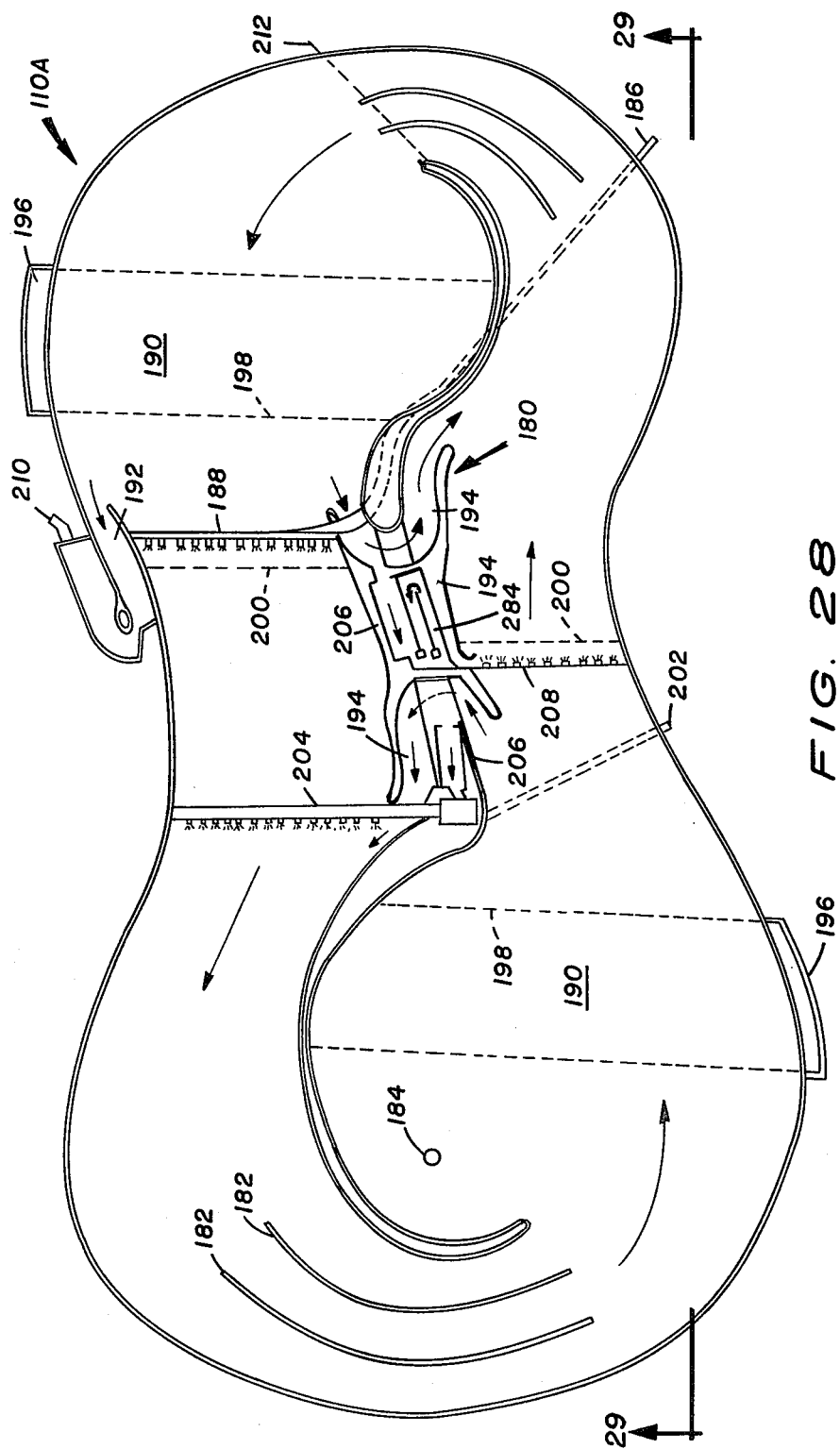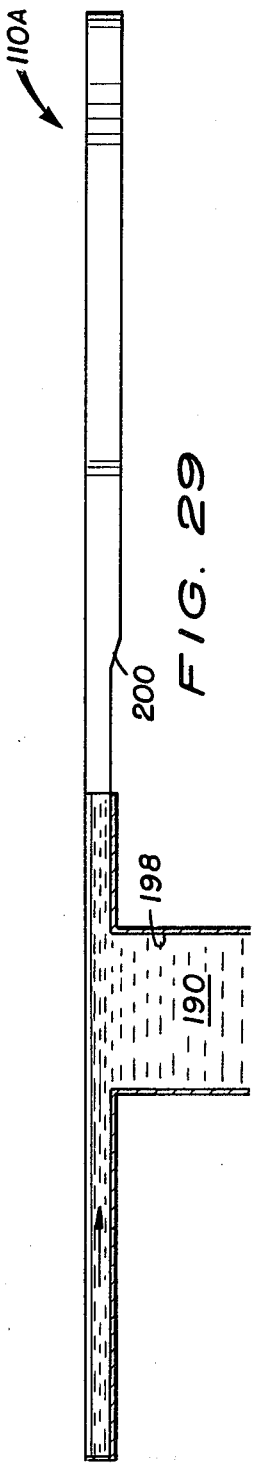

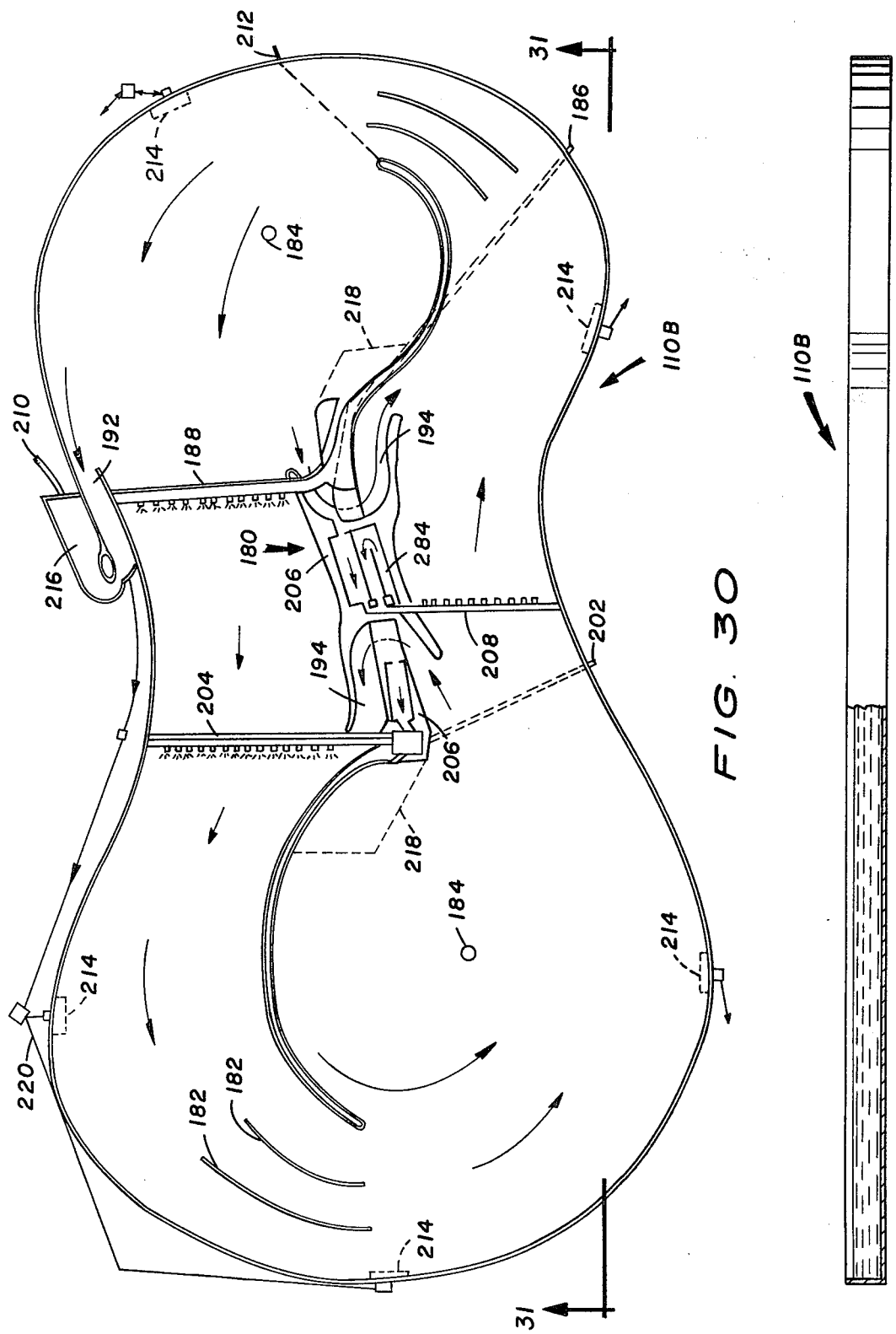

CONTROLLED NATURAL PURIFICATION SYSTEM FOR ADVANCED WASTEWATER TREATMENT AND PROTEIN CONVERSION AND RECOVERY

BACKGROUND AND SUMMARY OF THE INVENTION

The invention relates to wastewater treatment systems and in particular to wastewater treatment systems in which conversion of organic wastes and light energy to glucose takes place. Specifically, the invention relates to a complex system in which the wastewater and other associated discharges are treated anaerobically and aerobically in a tank complex where waste organics are reduced to inorganic forms available for algal culture in the uniquely designed rapid growth tanks.

Nitrate-nitrogen excessive to the aforementioned growth is removed by aerobic nitrification, anaerobic-denitrification filtration and aeration. Surplus phosphorus is taken out by precipitation and disposal. If algae farming is the objective, these excess nutrients will not be removed, but will also nourish the algae in an enlarged algal growth system. Hydrogen-sulfide gas and sulfides are reduced by anaerobic-aerobic treatment to sulfates to support algal growth. Odors are contained or eliminated in the closed system.

A need has existed for a long time for a system to treat organic wastewaters such as municipal sewage and effluents from food processing plants that economically could support its own operation. This invention provides such a system.

In conventional wastewater treatment systems certain standard or routine processes are utilized. Such conventional systems might include one or several of the following: screening to remove large objects and grit; degritting to remove sand, small stones, and coarse soil particles; comminuting to reduce particle sizes; skimming to remove floating solids, oils, fats, greases, and fuels; sedimentation to remove about 35 percent of the biochemical oxygen demand reduction and 50 percent of the suspended solids in the form of sludge; and flow equalization to store surges and feed them evenly to the process.

The aforementioned conventional processes are usually in a preliminary treatment given to wastewater and is usually determined by the individual characteristics of the wastewater. The various steps aforementioned are selected, sized and sequenced on an "as needed" basis and also as determined for the modes of treatment for further processing. In most conventional systems the subsequent treatment is primarily a treatment to prepare the liquid matter for release into a natural waterway.

In the present invention, the controlled natural purification system provides advanced wastewater treatment, protein conversion, and a recovery system of products for commercial use. As noted hereinbefore, settled wastewater is treated anaerobically and aerobically in a tank complex in preparation for algal growth. Also, as noted hereinbefore, the system of the present invention provides for removal of excessive nitrate-nitrogen and surplus phosphorus, reduction of hydrogen-sulfide gas and sulfides, and the containment or elimination of odors.

The process of the controlled natural purification (CNP) system provides rapid, cost-effective treatment of municipal or food plant wastewater by optimalizing the natural purification process: bacterial oxidation of organic wastes to produce stabilized nutrients (Step 1), for photosynthesis by microalgae (Step 2), and harvesting the algae by a 95% recovery process (Step 3). The resulting products are reusable water and a sterile, stable high-protein algal meal for poultry, swine, or cattle feed.

The invention provides new and novel combinations of sub-processes in reactor vessels and conduits. The Controlled Natural Purification System converts common municipal waste water and food processing plant effluent to reclaimable water and dried algae for use as animal feed. The sale of the algae for animal feed provides the economical advantage of the present invention to pay the cost of the construction and operation of the system. The system provides clean water, converts solar energy to a valuable product, and conserves energy in wastewater treatment. The invented system is such that it can be added to a conventional system as an extension of the prior art.

In natural purification, energy-yielding life processes as bacterial oxidation combine oxygen with organic wastes producing carbon dioxide, water, and energy.

In photosynthesis carried out by algae, energy is fixed as organic matter and oxygen is liberated.

In natural purification, the elements contained in organic matter are repeatedly oxidized and synthesized, gaining energy through the combination of light energy as they pass up the food chain until death and recycle. If the goal of natural purification is recycle, the goal of the Controlled Natural Purification process is controlled recycle. The products of algae meal and reclaimable water become available for recycle at their highest commercial use.

The settled wastewater in the Controlled Natural Purification process is treated for 16 to 24 days in the tank complex (shown in this invention as the B-tank complex) where the waste organics are reduced in carbonaceous and nitrogenous stages to inorganic nutrient forms available for algal growth. Solids in the B-tank anaerobic filters are treated until decomposed.

Bacterial oxidation of organic wastes is completed in sun-lighted tanks (shown in this invention as the A-tank complex) in an $O_2$-$CO_2$ bacterial exchange with algae. The algae photosynthetically metabolize the bacteria-converted nutrients in the $CO_2$-enriched culture liquid during two to twelve days retention. The supplemental $CO_2$, diffused throughout the biomass is a 5% mixture in air, is mostly a by-product of B-Tank aerobic decomposition, and of combustion of hydrocarbon fuels used in algae drying, including process-produced methane. Additional commercially supplied $CO_2$ is furnished as required.

A biologically-effective light is the limiting factor in the A-tanks, all other variables are aligned to produce maximum algal yield and high effluent quality. After removal of the algae the effluent meets advanced treatment standards. In this final stage, 95% of the algae are separated, concentrated, dewatered, and dried for market.

The removal of sludge and its treatment from raw effluent is a more or less common procedure and is not a part of this invention. This invention deals with the settled wastewater of municipal sewage and organic industrial wastewater such as food plant effluent.

The efficiency of conversion of solar energy to photosynthate has a conservatively projected efficiency in the Controlled Natural Purification reactor of the system of 3.5 percent of bioeffective sunlight, or 1.4 percent of total solar insolation. This conservatively projected efficiency for a parallel at Washington, D.C. and vicinity will produce on a yearly average 9.25 grams per square meter per day of ash-free dry algae, or between 16 and 17 tons per acre per year of dry algae (15 percent ash content). Annual yields will vary at other locations, with available amounts of bioeffective solar radiation.

While this invention proposes the growth of algae for animal feeds (poultry, swine, and cattle), the use of algae for aquaculture, for pharmaceuticals, extraction of pigments (such as chlorophyll and xanthophyll) and for bioconversion to fuels by the use of the system (as well as other technical, medicinal, nutritional, and industrial uses) all are within the scope and intent of this invention.

Algae, in addition to containing 40 to 70 percent protein, is relatively high in xanthophyll. Xanthophyll is a pigment used in poultry diets to impart the desirable yellow color to the skin of the boiler and the egg yolk of the laying hen (dark yellow egg yolks are in demand by the noodle industry). The pigment at present must be derived from natural resources such as corn gluten meal, or marigold meal imported from Mexico and Equador. As to the protein content, algae meal compares favorably with soy bean meal.

Algae as a fuel compares favorably with medium-grade coal: one pound of algae has a heating equivalent of 10,000 BTU's while one pound of medium-grade coal is 12,000 BTU's (or by comparison, the heating capacity of six tons of algae equals that of five tons of medium-grade coal).

Algae can be fermented to produce marsh gas which is 78% methane gas, a fuel with a heating equivalent of 995 BTU's per cubic foot (natural gas is 95 percent methane). One ton of algae will produce about 18,000 cubic feet of methane to produce 2000 to 4000 Kwh of steam-generated electric power, or fermentation of algae can be arrested at the acid-forming stage, producing organic acids which can be processed to alcohol.

The aforementioned food and fuel possibilities of the present invention are presented to point out the economics and energy conservation aspects of the Controlled Natural Purification system of this invention.

Regarding aquaculture, the possibility of algae production through this invention provides the potential for development of an aquaculture industry for fish farming and other related food means (such as tilapia, as fast-growing herbivorous [algae-eating] fish).

Controlled Natural Purification system treatable wastewater is a continuously replenishable resource which, when exploited, diminishes the triple threat to civilization of pollution, shortage of food, and shortage of water. In a like manner, it provides even more tangible benefits to the public in the threats of energy shortage and high food costs. An additional benefit can be tax reduction by reason of the selfsupporting operation of the Controlled Natural Purification system, as well as amortizing the original construction cost.

Food processing companies would also benefit from the recycling investment tax credit (currently 10%, in addition to 10% investment tax credit). When operated for extensive algae farming on organic wastewater of one-third the U.S. population and the food processing plants, the Controlled Natural Purification system could annually produce an estimated ten million tons of high-protein algae on less than one-tenth the acreage now required for soy bean production.

As aforementioned, certain preliminary treatments to the wastewater removes certain ingredients in sludge form so that settled wastewater becomes available for processing in the Controlled Natural Purification system. The removal of these ingredients reduces sludge build-up in the reactor of the system which would require frequent sludge wasting and cleanout of anaerobic filters. Such sludge removal is usually by sedimentation or air flotation.

As noted hereinbefore, the sludge receives separate treatment and is not a part of this invention. That part of any municipal sewage sludge that remains in the Controlled Natural Purification integrated system is processed and disposed by means such as high-rate anaerobic digestion, drying, and landfill. The by-products of the high-rate digesters, methane and carbon dioxide, support the Controlled Natural Purification process (combustion of methane gas provides heat for digesters and partial heat for algae drying).

Any waste heat available, from any source, can be used to heat the settled influent by means of heat exchangers in equalization tanks (shown as E-tanks in the Controlled Natural Purification system), in order to improve the efficiency of the Controlled Natural Purification anaerobic filters.

It is, therefore, an object of the invention to provide a Controlled Natural Purification system to remove from wastewater, by conversion to their nutrient chemical forms, organic wastes that exert biochemical oxygen demand.

It is another object of the invention to provide a Controlled Natural Purification system to maintain a nutrient balance with the optimum light-energy conversion factor.

It is also an object of the invention to provide a Controlled Natural Purification system to use light efficiently so that as many cells as possible are exposed to light and dark for optimal time, at optimal temperature, at economically acceptable cost.

It is also still another object of the invention to utilize supplemental pulsed lighting to significantly increase algae growth by satisfying the algae desire for the light between midnight and the pre-dawn hours.

It is still another object of the invention to provide a Controlled Natural Purification system to deliver, after algae removal, cost-effective, reclaimable water that meets advanced treatment standards.

It is yet another object of the invention to provide a Controlled Natural Purification system to harvest 95 percent of the algae generated.

It is also another object of the invention to provide a Controlled Natural Purification system to dry the algae in a manner to produce a stable, high-quality, commercially-valuable product.

It is yet still another object of the invention to provide a Controlled Natural Purification system to achieve maximum energy savings compared to conventional treatment systems.

It is also still another object of the invention to provide a Controlled Natural Purification system to achieve maximum financial savings compared to conventional treatment systems.

Further objects and advantages of the invention will become more apparent in the light of the following description of the preferred embodiments.

BRIEF DESCRIPTION OF THE DRAWINGS

FIG. 3 is a plan view of the general layout of the B-Tank complex of FIG. 2;

FIG. 4 is a cross sectional view on line 4—4 of FIG. 3;

FIG. 5a is a plan view of A-Tank relationships from A-1 through first embodiment of A-6;

FIG. 6 is a cross sectional view on line 6—6 of FIG. 5a;

FIG. 13 is a partial cross sectional view of anaerobic filters;

FIG. 14 is a plan view of an element of the A-1 Tank;

FIG. 15 is a side view on line 15—15 of FIG. 14;

FIG. 16 is a side view on line 16—16 of FIG. 14;

FIG. 17 is a cross sectional view on line 17—17 of FIG. 14;

FIG. 18 is an open channel section on line 18—18 of FIG. 14;

FIG. 23 is a plan view of light cluster tanks;

FIG. 24 is a side view on line 24—24 of FIG. 23;

FIG. 25 is a side view on line 25—25 of FIG. 23;

FIG. 26 is a side view of a light cluster;

FIG. 27 is a cross sectional view on line 27—27 of FIG. 26;

FIG. 28 is an enlarged plan view of a first embodiment of an A-6 Tank;

FIG. 29 is a cross sectional view on line 29—29 of FIG. 28;

FIG. 30 is an enlarged plan view of a second embodiment of an A-6 Tank;

FIG. 31 is a cross sectional view on line 31—31 of FIG. 30;

DESCRIPTION OF THE PREFERRED EMBODIMENT

Figure 1:
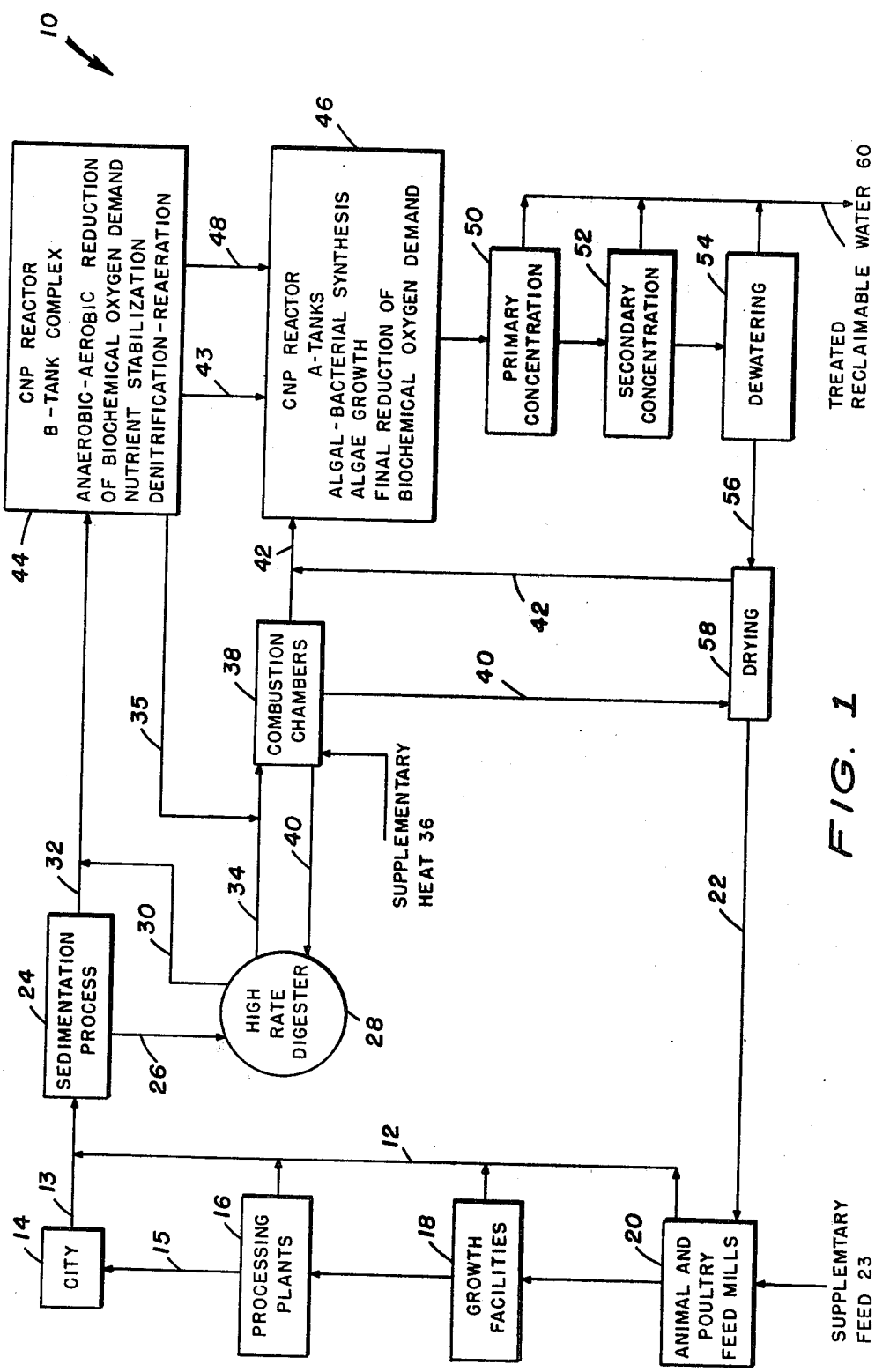
FIG. 1 is a schematic diagram of an integrated system of a controlled natural purification system.

Referring to the drawings and particularly to FIG. 1, a controlled natural purification system for advanced wastewater treatment and protein conversion and recovery is shown in schematic form at 10.

In the schematic diagram of FIG. 1 the sources of raw wastewater 12 can be seen at the left side of the drawing. The sources of raw wastewater 12 are illustrated as coming from the city 14 in general sewage 13 plus raw wastewater 12 from processing plants 16, growth facilities 18, and animal and poultry feed mills 20.

The indication of the processing plants 16, growth facilities 18, and feed mills 20 is for illustrative purposes and specifically selected as these are typical of such plants and facilities as would use the algae meal 22 that result from the present invention of a Controlled Natural Purification system 10. It is to be understood that many other type plants and facilities would produce raw wastewater 12 that would flow to the CNP system 10, separately or within the general sewage 13. Supplementary feed 23 is mixed with the algae meal 22.

It is to be understood that the system of this invention may be used for municipal installations or for private enterprise facilities to process raw wastewater 12.

As previously described hereinbefore, the combined raw wastewater 12 and general sewage 13 goes through a sedimentation process 24 to remove various solids and other matter as sludge 26. The sedimentation process 24 involves settling of suspended solids and removal of non-settable substances rendered settleable by coagulation or precipitation, as well as screening, degritting, comminuting, and skimming as aforesaid. These operations are common to most conventional wastewater or sewage treatment systems.

The sludge is digested in a high-rate digester 28 which generally prepares the sludge 26 for disposal by suitable means. During the digestion a supernatant liquor 30 develops that ordinarily might be disposed of by suitable means in a conventional wastewater treatment system. This supernatant liquor 30 in the process of the present invention is transferred to and mixed with the settled wastewater 32 moving from the sedimentation process 24. The supernatant liquor 30 at this point has a highly soluble concentration of carbonaceous oxygen demand.

The combined settled wastewater 32 and the supernatant liquor 30 at this point enter the Controlled Natural Purification system 10. The entry of this combined mixture into the Controlled Natural Purification system 10 is at the aforementioned B-Tank complex 44 in FIG. 1.

Referring again to the high rate digester 28, a useable gas 34 (methane 78%, $CO_2$ 22%) is generated during the operation of the high rate digester 28. This useable gas 34, in combination with a supplementary heat means 36, is used in combination chambers 38 to produce heat 40 and $CO_2$ gas 42. The heat 40 is used to operate the high rate digester 28 and the $CO_2$ gas 42 is used in the operation ($CO_2$ enrichment) of the aforementioned A-Tanks 46 in FIG. 1, described later in detail.

The B-Tank complex 44 and the A-Tanks 46 are each essentially a Controlled Natural Purification Reactor. The B-Tank complex 44 provides anaerobic and bacterial oxidation of the organic wastes, a reduction process, in which there is nutrient stabilization, nitrification, denitrification and reaeration. During this B-Tank complex 44 operation, additional useable gas (methane 78%, $CO_2$ 22%) 35 is generated which is directed to and combined with the useable gas 34 coming from the high rate digester 28. In addition, $CO_2$ gas 43 is also generated which is directed to the A-Tanks 46 for combination with the $CO_2$ gas 42 in a 5% mixture in air compressed to six pounds per square inch.

The important results of the operation of the B-Tank complex 44 is the production of a culture liquid 48 that is transferred to the A-Tanks 46.

The A-Tanks 46 arrangement provides an algal-bacterial synthesis resulting in algae growth and a final aerobic bacterial oxidation of the organic wastes, a reduction process.

Effluent from the A-Tank 46 operation produces a primary concentration 50 and therefrom a secondary concentration 52 therefrom of harvested algae. The harvested algae then goes through a dewatering stage 54 and the solids 56 passing through a drying stage 58 to produce algae meal 22. Flowing from the primary concentration 50, the secondary concentration 52, and the dewatering stage 54 is another by-product, treated reclaimable water 60.

The algae meal 22 passes into the commercial stage for uses as hereinbefore mentioned, such as, but not limited to, animal and poultry feed, aquaculture, fuel, pharmaceuticals, and other similar uses. A selected illustration in FIG. 1 indicating the use of algae meal 22 (with supplementary feed 23) in animal and poultry feed mills 20, subsequent use of the feed in growth facilities 18 for animals and poultry, and subsequent use of the algae meal fed animals and poultry in processing plants 16. The supplementary feed 23 consists of grain, alphalfa, fish meal, and similar food stuff. Other protein products 15 from the same system flow to the city for consumption, thus the cycle is completed in which the present invention is a key link.

Directional arrows in FIG. 1 indicate the flow pattern as hereinbefore described.

In the spcifications which follow, the details of the Controlled Natural Purification system for advanced wastewater treatment and protein conversion and recovery 10 are provided. These details primarily deal with the B-Tank complex 44, the A-Tanks 46, and the harvesting of the algae at the primary and secondary concentrations 50 and 52.

Figure 2:
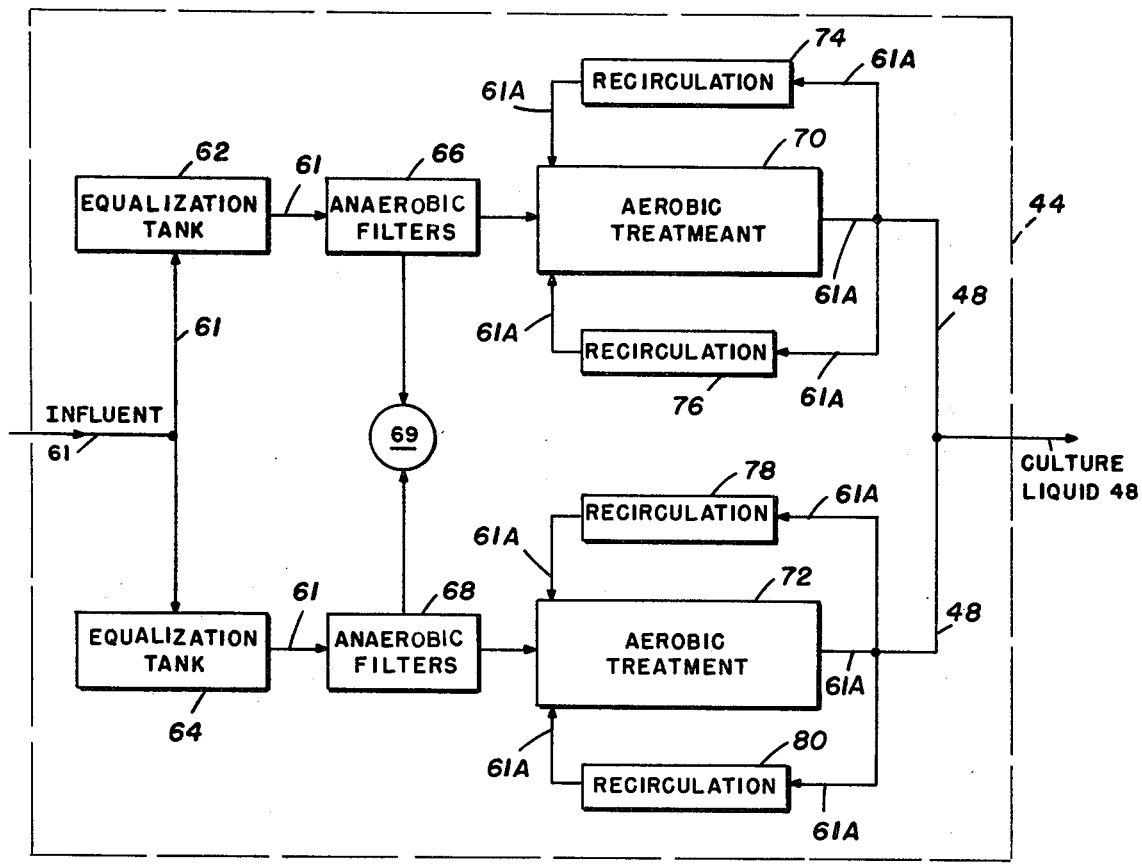
FIG. 2 is a schematic diagram of a B-Tank complex of a controlled purification system.

Referring now to FIG. 2, a schematic diagram of the B-Tank complex 44 of FIG. 1 indicates the processes that take place in the B-Tank complex 44 arrangement.

As seen in FIG. 2, the influent 61, which is a mixture of the supernatant liquor 30 and the settled wastewater 32, enters at the left for this illustrative specification. For illustration, an influent 61 of one million gallons per day (1MGD) is used in order to demonstrate the division of the flow in the process.

It is to be understood that the system of this invention may be any size to handle a range of capacities and biological loadings. The illustrated one million gallons per day is for explanatory purposes only.

The first passage of the influent 61, after entering the B-Tank complex 44, is routed into equalization tanks 62 and 64. The distribution is essentially one-half to equalization tank 62 and one-half to equalization tank 64 to equalize the flow rate.

The equalization tanks 62 and 64 are the initial storage of the influent 61 entering the B-Tank complex 44, in addition, this initial storage permits the temperature to also equalize.

As to the temperature differentials, it is recalled that the influent 61 is a mixture from two sources: from the sedimentation process 24 as settled wastewater 32 and from the high rate digester 28 (the latter in the form of supernatant liquor 30). The processes by their very nature have the potential of producing discharges of varying temperatures. As noted, the equalization tanks 62 and 64 provide the means for the temperatures to equalize before the next step in the B-Tank complex 44.

From the equalization Tanks 62 and 64 the next flow is into a series of anaerobic filters 66 and 68. Note that in FIG. 2 only a single box is shown to schematically illustrate the anaerobic filters 66 and likewise for the anaerobic filters 68. As will be shown later, there is a plurality of anaerobic filters 66 and 68.

A collection means 69 for methane gas generated in and by the anaerobic filters 66 and 68 collects the methane gas for transfer to gas used in the combustion chambers 38 as hereinbefore described.

It is in the B-Tank complex 44 where the waste organics are reduced in carbonaceous and nitrogenous stages to inorganic nutrient forms available for algal growth. Nitrate-nitrogen excesive to such growth is removed by anaerobic denitrification filtration and aeration. Surplus phosphorus taken out by precipitation and disposal. Hydrogen-sulfide gas and sulfides are reduced by anaerobic-aerobic treatment; odors are contained or eliminated in the closed system.

Following the flow from the anaerobic filters 66 and 68, the influent 61 to the B-Tank complex 44 flows in equal amounts from each plurality of anaerobic filters 66 and 68 into the aerobic treatment tanks 70 and 72. In this phase aerators (such as air guns, described later) bubble or aerate air through the influent 61 as it passes through the aerobic treatment tanks 70 and 72.

It should be noted at this point that, as aforesaid, one million gallons per day is being used as a typical example of influent 61 entering the system. The controlled natural purification system 10 may be developed to accept a range of volumes of influent 61. However, it is also to be noted that initially there will be an initial charge of influent 61 required to set the system in motion.

As the influent 61 passes into the aerobic treatment tanks 70 and 72, essentially one-half of the one million gallons per day to each tank, the influent 61 in each tank is joined by and mixed with 250,000 gallons per day in each tank of recirculated influent 61A, the influent 61A being influent 61 after partial treatment. Initially, this recirculated influent 61A would be from the aforesaid initial charge of influent 61.

As the combined influents 61 and 61A pass through the aerobic treatment tanks 70 and 72 the total of 750,000 gallons per day leaves each of the aerobic treatment tanks 70 and 72 (500,000 from the influent 61 and 250,000 gallons from the recirculated influent 61A).

The 750,000 gallons per day leaving each aerobic treatment tank 70 and 72 is now divided into three paths: 125,000 gallons is recirculated through each of two recirculation tanks 74 and 76 (or 78 and 80) parallel to the aerobic treatment tank 70 (or 72); and 500,000 gallons flow out of each tank 70 and 72 of the B-Tank complex as culture liquid 48 for the next series of processes in the A-Tanks 46. Thus, as one million gallons per day of influent 61 enter the B-Tank complex 44, so one million gallons per day of culture liquid 48 leave the B-Tank complex 44 process (500,000 gallons from each of the aerobic treatment tanks 70 and 72).

Thus, in the overall B-Tank complex 44 operation, 50 percent of the influent 61 is recirculated to improve the quality and to evenly distribute the biological loading in the A-Tank complex 46.

Directional arrows in FIG. 2 indicate the direction of flow through the B-Tank complex 44.

The recirculated influent 61A may be routed through one or more anerobic filters 86, 88, 90 and 92 (FIG. 3), if there is: first, a high build-up of suspended solids, the filters functioning with acid-forming and methane-forming bacteria to produce methane to support the system; and/or, second, a nitratenitrogen surplus to algae growth needs (e.g., in winter when the photosynthetic process slows), one or more filters are used as anaerobic denitrification filters, with denitrifying bacteria to convert nitrates to nitrogen gas, which is released from solution and vented to the atmosphere after reaeration in one or more recirculation Tanks 74, 76, 78 and 80.

As to temperature of influent 61, the temperature will be normally stabilized in the equalization tanks 62 and 64 at about 60° F. Where necessary, heat exchangers can be installed in the equalizaton tanks 62 and 64 to control the temperature. Waste heat from the system or from other sources for the temperature control may be used.

As will be described later, the recirculation tanks 74, 76, 78, and 80 have baffles therein to cause the influent 61A to flow in an alternating pattern over one baffle and then under the next.

Before describing the details of the B-Tank 44 structure, there follows a generalization of the A-Tanks 46 arrangement.

The A-Tanks 46 range in number from one to a plurality of six or more. For descriptive purposes the A-Tanks 46 are shown as: A-1, A-2, A-3, A-4, A-5 and A-6 (first, second and third embodiments). Essentially, tanks A-2 through A-5 are of similar configuration and structure, as hereinafter described, and the A-6 are of another configuration and structure as hereinafter described. The differences occur in: positioning of each A-Tank in relation to the B-Tank complex 44; the process that occurs in each A-Tank; the number of each type A-Tank used in the system established for a specific purpose or need; and the flow pattern used for processing the wastewater through the various A-Tanks in the arrangement.

In effect, each of the various combinations and arrangements represent an embodiment of the Controlled Natural Purification process. The end product is essentially the same from all combinations. The combination and arrangement used is developed for the requirements of each need and related to the capacity necessary to handle the volume of wastewater to be processed.

The B-Tank complex 44 is a covered system to contain heat, gas and odors. The heat and gas utilized later in the operation and the odors are treated for elimination. It may be set within the ground, set into a hillside, have an earth berm-like mound built up around the structure if set above normal ground level, or a combination of these means. In this specification the B-Tank complex 44 will be shown set into the ground in whole or in part.

The A-1 Tank is set on top of the B-Tank complex 44. The A-1 Tank serves as a cover for the B-Tank complex 44 and concurrently holds the heat within the enclosure. The A-1 Tank is essentially level. The A-2 through A-5 tanks are preferably set on a hillside so that a natural flow is obtained for the wastewater being processed. An artificial hill-like means may be used or a pumping system. In this specification the A-2 through A-5 tanks will be shown on a hillside.

The A-6 tank portion of the process may be one tank or a plurality of tanks. If a plurality of A-6 tanks is used they may be connected in series or in parallel.

As to the aforesaid embodiments, based on the needs for the system, the system may consist of a B-Tank complex 44 (used in all embodiments) and one or more of the A-Tanks. The simplest, for a small volume requirement, would use only the A-1 Tank. Others would use: A-1 and A-2 Tanks; A-1, A-2, and one or more of the A-3 to A-5 Tanks; any of the preceding combinations and one or more A-6 Tanks.

It is to be noted that in an extremely large system which might have an exceptionally large B-Tank complex 44, or several B-Tank complexes to service the system, more than one each of tanks A-1 through A-5 could be used to handle the wastewater being processed from the large B-Tank complex 44 in the system.

For this invention the system will be described as consisting of a B-Tank complex 44 and an A-Tank Complex 46 having an A-1 Tank on top of the B-Tank Complex 44, A-2 through A-5 tanks on a hillside, and a plurality of A-6 tanks.

Following hereinafter the details of the B-Tank Complex 44, the details of the A-1 through A-5 tanks, and the details of the A-6 tank, including the flow through the various tanks and in both A-6 tanks in series and in parallel, will each be described.

Referring now to FIGS. 3 and 4, FIG. 3 is a plan view of the general layout of the B-Tank Complex 44. As has been described for FIG. 2, the influent 61 first passes into the equalization tanks 62 and 64 as hereinbefore described. The directional arrows indicate the directional flow of the wastewater being treated, the directional flow is shown for both piping between tanks and other units and within tanks (such as tanks 70, 72, 74, 76, 78 and 80).

As shown by the directional arrows, the influent 61 is directed by piping into the equalization tanks 62 and 64 and then, as shown by the directional arrows, the influent 61 passes out of the equalization tanks 62 and 64 and into a plurality of anaerobic filters 66 and 68 (three shown on each side for purposes of illustration). It is to be understood that the matter of numbers of units in this specification, such as the anaerobic filters 66 and 68 and other units hereinafter to be specified, are for illustrative purposes and the exact number of units for any system will depend on the capacity requirements of the system concerned. Note that in the matter of the piping with directional arrows that if desired or warranted, the influent 61 may be shunted past the equalization tanks 62 and 64 by closing valves 63 and 65 and opening valve 67.

From the anaerobic filters 66 and 68 the influent 61 is piped into the mixing chambers 82 and 84 to mix with partially processed influent 61A being recirculated through recirculation tanks 74, 76, 78, and 80. The mixture of influent 61 and partially processed influent 61A then passes through the B-Tanks 70 and 72 as hereinbefore described.

As hereinbefore described, 50 percent of the influent 61 and 61A passing through the B-Tanks 70 and 72 is recirculated, 25 percent through each tank 70 and 72 are therefrom recirculated in equal proportion through the recirculation tanks 74, 76, 78, and 80. The processed influents 61 and 61A that leave the B-Tank complex 44 pass out as culture liquid 48.

The recirculation through recirculation tanks 74, 76, 78, and 80 is for the purpose of improving the quality and to evenly distribute biological loading in the A-Tank complex 46, hereinafter described.

In the winter when photosynthetic process slows, the recirculated effluent 61A is routed through the anaerobic denitrification filters and reaerated to remove nitrogen excessive to algal growth. The winter flow directions are shown for B-Tank 70, the summer flow directions are shown for B-Tank 72. The piping system permits both tanks to be set for either the summer or winter flow arrangement. The directional arrows in FIG. 3 indicate the flow for each hook-up.

For the winter set (B-Tank 70 for illustration) the influent from the B-Tank 70 flows into the effluent chamber 94 from where the portion to be recirculated flows into anaerobic denitrification filters 86 and 88. It can be seen that at the point where the influent flows into the anaerobic denitrification filters 86 and 88, a portion also flows out as culture liquid 48. From the anaerobic denitrification filters 86 and 88 the influent is piped back into the recirculation tanks 74 and 76.

For the summer set up (B-Tank 72 for illustration) the influent from the B-Tank 72 flows into the effluent chamber 96 from where it bypasses the denitrification filters 90 and 92 and flows directly to the recirculation tanks 78 and 80.

In the aforementioned winter and summer set ups, the direction of flow of the influent from B-Tanks 70 and 72 to the recirculation tanks 74, 76, 78, and 80 is controlled by the valve system on the pipes. The valve settings are as described hereinafter.

For the winter set up valves 71 are closed and valves 85 and 87 are opened, thus permitting the influent to circulate through the anaerobic denitrification filters 86 and 88.

For the summer set up valves 89 and 91 are closed and valves 73 are opened, thus the influent bypasses the anaerobic denitrification filters 90 and 91.

From the valve arrangement shown in FIG. 3, it can be seen that both B-Tanks 70 and 72 can be set up for either the summer or winter process.

Valves 47 permit the control of the flow of the culture liquid 48 in conjunction with the other valves so as to maintain the objective of 50% recirculation. This valve arrangement also permits modifying this flow to other proportions if the conditions warrant a change.

It is to be understood that the valve arrangement and the control of the flow throughout this invention may be automated and such an automated control is within the scope and intent of this invention.

It is also to be noted that only essential valving is being mentioned for process description purposes and is not to be construed as the only valves in such a process. Under normal fabrication all piping lines would contain valve controls so that sections could be isolated for repairs and maintenance and the like, but which are not essential to describing the process of this invention.

Because of negligible heat loss in the B-Tank Complex 44, temperatures, generally, will stabilize at influent levels at or above 60° F. Influents below that level should reach the 60° F. equilibrium, the approximate temperature of surrounding earth and A-1 Tank cover. When waste heat is available, heat exchangers may be used in the equalization tanks 62 and 64.

It is to be noted that the B-Tanks 70 and 72 control the A-Tanks dilution rate. The rate of the B-Tanks treated effluent controls the A-Tanks dilution rate which is correlated with the intensity of the sun. This control requires storage of about one million gallons (in the aforementioned cited example) of treated water in the B-Tanks 70 and 72 over a 24 hour period, thus resulting in a fluctuating water level in the B-Tanks.

In FIGS. 3 and 4 aerators 98 provide means for reaerating the influents 61 after denitrification in the denitrification filters 86 and 88 (and 90 and 92) in the winter hook-up.

Regarding the process of this invention, it is to be noted that natural purification is the repeated oxidation and synthesis of elements contained in organic matter through combination of light energy as they pass up the food chain until death and recycle.

The controlled natural purification (CNP) process is based on the concept that organic wastewater is a renewable resource and that its treatment produces income. The controlled natural purification process follows the natural purification cycle in three regulated steps: first bacterial oxidation of organic wastes exerting biochemical oxygen demand (BOD), to produce stabilized nutrients, for the second step, the photosynthesis by microalgae, for the third step, the harvest of the product for animal feed.

Figure 5B:
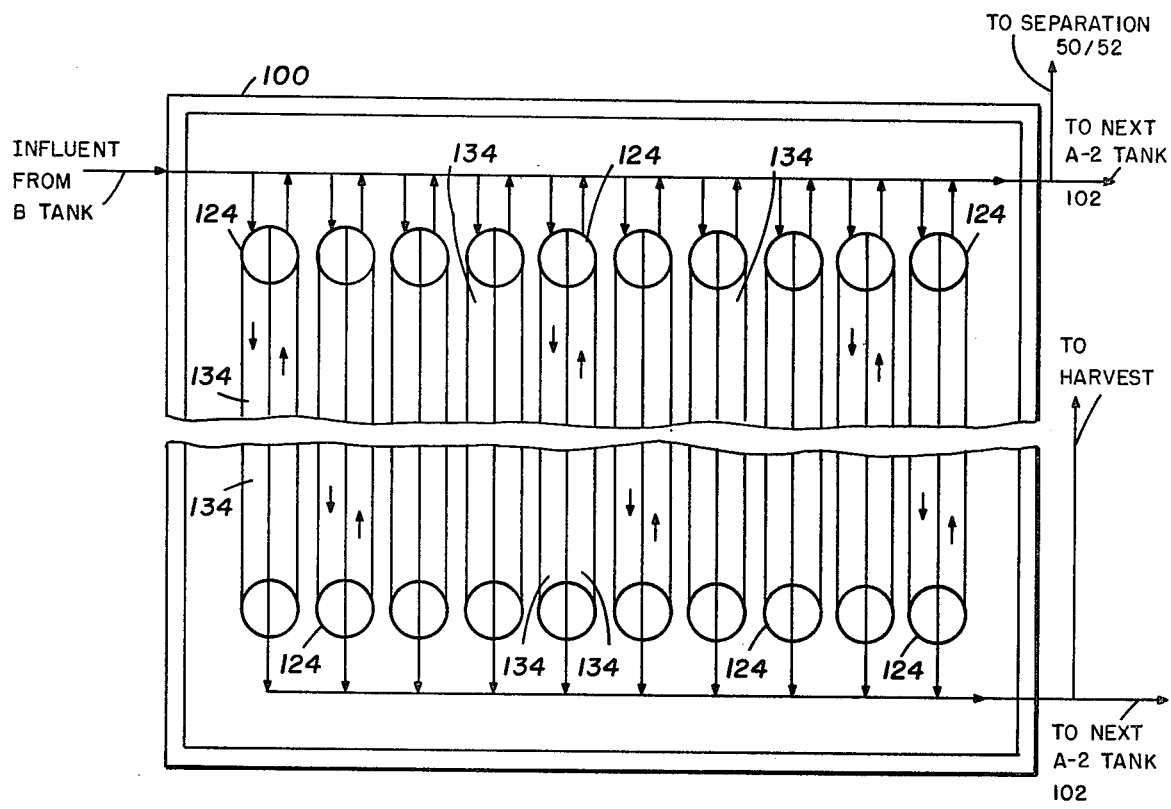
FIG. 5b is a plan view of the A-1 tank showing piping.

Referring now to FIGS. 5a and 6, FIG. 5a shows the A-1 tank 100 installed on top of the B-Tank Complex 44. It is to be noted that for this illustration of the invention that the B-Tank complex 44 is shown built partially below the normal grade 120 in the general area, and is then covered around the sides by a berm-like mound 122, as hereinbefore mentioned.

Except for slight inclines in each longitudinal direction from the lateral centerline to facilitate drainage from precipitation, the A-1 tank 100 is substantially level as installed across the top of the B-Tank complex 44. As hereinbefore mentioned the A-2 through A-5 complex of tanks is best suited on an artificial incline or a hillside for operation, this can be seen in FIG. 6. In FIG. 6 the A-2 tank 102, A-3 tank 104, A-4 tank 106, and A-5 tank 108 are shown in descending order on a hillside. The A-6 tank 110 is shown at essentially grade level 120.

FIGS. 5a and 6 for what may be termed an operational mode, are somewhat schematic and the details for the A-Tank Complex 46 (which includes A-1 tank 100 through A-6 tank 110) will be described hereinafter. It is to be understood that, depending on the size of the operation for the volume of wastewater to be handled, a larger array of A-tanks A-2 through A-5 may be used, the array used here is to illustrate the invention. Likewise, it is to be noted that the A-Tanks A-2 through A-5 are exactly alike and the description of one describes each of them.

The A-1 tank 100 is substantially like the A-2 through A-5 tanks and performs a similar function, except that being set at a more or less level grade over the B-Tank Complex 44 it has some differences in operation.

Similarly, in FIGS. 5a and 6 only one A-6 tank 110 is shown, but there may be several A-6 tanks 110 (or with some variations as will be described hereinafter) to handle variations in volume of wastewater. As hereinbefore mentioned, the A-6 tanks 110 may be set in an array in series or an array in parallel, these variations will also be described hereinafter.

The depiction of the A-1 tank 100 and the A-2 tank 102 through the A-5 tank 108 is a plan view in schematic format. The details of certain elements of the structure will be described in later drawings and specification. For the present, FIGS. 5a and 6 will be used to show the relationship of the various A-tanks to each other.

The plan view of the A-1 tank 100 in schematic format is shown in FIG. 5a and in FIG. 6 the A-1 tank 100 is shown in cross sectional schematic format on top of the B-Tank Complex 44, note that the general cross-section is level. In a like manner the plan view of the A-2 tank 102 through the A-5 tank 108 in schematic format is shown in FIG. 5a and in FIG. 6 the A-2 tank 102 through the A-5 tank 108 is shown in cross sectional schematic format on a hillside.

The plan view of one A-6 tank 110 in schematic format is shown in FIG. 5a and in cross sectional schematic format a grade level in FIG. 6. For illustration of the invention at this point only one A-6 tank 110 is shown, but it is to be noted as previously described there can be several A-6 tanks connected in series or in parallel. More will be described about this arrangement later.

Regarding FIGS. 5a and 6, flow of liquid in the A-1 through A-6 tanks is indicated by directional arrows. More detail on the structures that carry the liquid will be provided later.

Also shown in FIGS. 5a, b, c is a schematic diagram of one embodiment of piping connections. It is to be noted that various piping arrangements can be established for directing or controlling the flow of liquid in the system at all locations.

Regarding the piping as shown in FIGS. 5a, b, and c, the ends of each of the transverse runs has a control tank 124 for directing the influent to the next directional flow that it is to make. The details of these control tanks 124 will be described hereinafter, but it is to be noted that the piping system manifolds all of them together on each side of each segment of the tank system. This manifolding provides means for bypassing any element of a tank segment, or bypassing an entire tank segment (such as the A-2 tank 102 or the A-4 tank 106) for repairs or maintenance, provides means for drawing off settled old algae to harvest, routing culture liquid to the next tank segment, and numerous other servicing operations.

In FIG. 5a the relationship of the A-Tank Complex 46 to the subsequent operation of separation 50 and 52, dewatering 54, drying 58, and production of algae meal 22, is shown to the side of the A-tank array.

The preceding description provides the general description of the system, however, there are some special details that must be described in order to completely cover the system. Some of these descriptions concern the B-tank Complex 44 and some concern the A-tank Complex 46.

Figure 7:
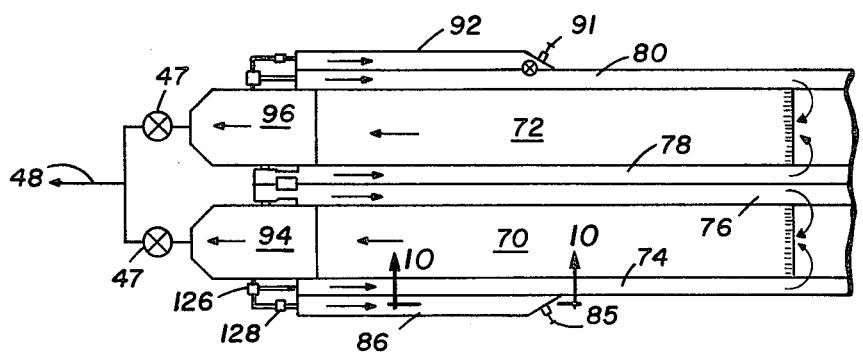
FIG. 7 is a partial flow pattern through B-Tank complex showing alternate embodiment.

In the schematic plan view of the B-Tank Complex 44, shown in FIG. 3, the anaerobic denitrification filters 86, 88, 90, and 92 were shown in a first embodiment at the ends of the B-Tank 70 and B-Tank 72. An alternate embodiment is to place the anaerobic denitrification filters along the side of the recirculation tanks. An embodiment showing such an arrangement is provided in FIG. 7. Note, however, that this reduces the number of anaerobic denitrification filters in FIG. 3 from four (86, 88, 90, and 92) to two (86 and 92). For clarity, the same identification numbers used in FIG. 3 have been used in FIG. 7. No anaerobic denitrification filters are shown in FIG. 7 for recirculation tanks 76 and 78. Valve controls for the summer and winter hook-ups of the anaerobic denitrification filters for the inlet ends to the anaerobic denitrification filters 86 and 92 and the recirculation tanks 76 and 78 are not shown. As will be shown hereinafter in FIGS. 8, the control for the latter flow for this embodiment is through a special pump and manifold.

Figure 8:
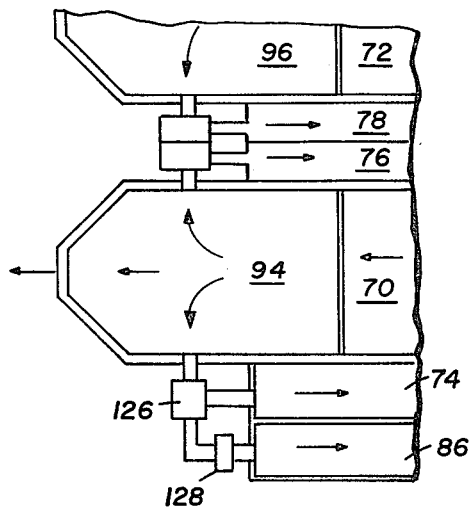
FIG. 8 is an enlarged view of a portion of FIG. 7.

In FIG. 8 the manner of controlling the flow to the recirculation tank 74 and the anaerobic denitrification filter 86 is shown as a control pump 126. Between the control pump 126 and the aneaerobic denitrification filter 86 is an inoculum and chemical unit 128.

Figure 9:
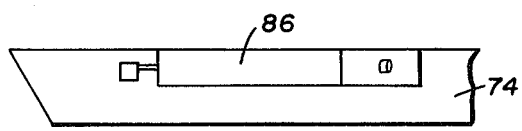
FIG. 9 is a partial side view of FIG. 7.
Figure 10:
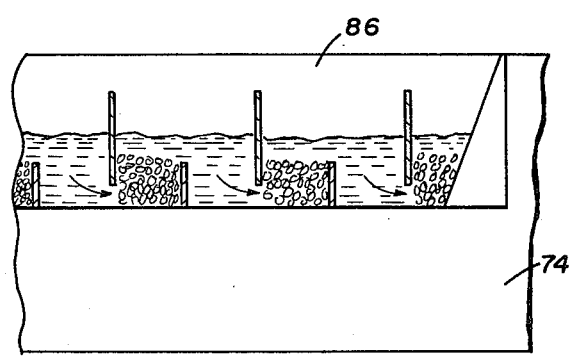
FIG. 10 is a partial enlargement of a cross sectional view on line 10—10 of FIG. 7.

A side view of FIG. 7 is shown in FIG. 9. The anaerobic denitrification filter 86 is shown on the side of the recirculation tank 74. In FIG. 10 a portion of the baffle system in the anaerobic denitrification filter 86 can be seen in cross section.

Figure 11:
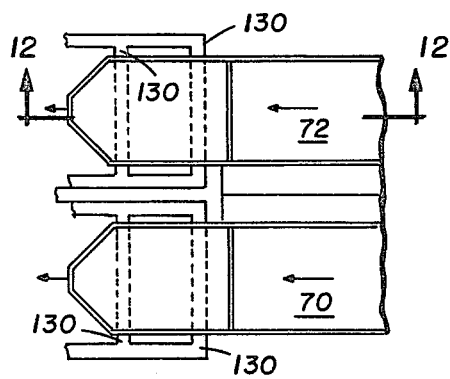
FIG. 11 is a plan view of a sludge draw-off system.
Figure 12:
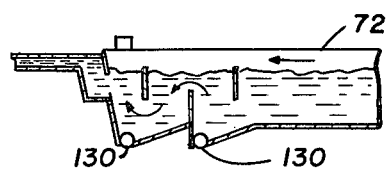
FIG. 12 is a cross sectional view on line 12—12 of FIG. 11.

As sludge accumulates in various places in the controlled natural purification system 10, the sludge must be removed. One of the places it will accumulate is at the outlet end of B-Tanks 70 and 72. A vacuum draw-off system is incorporated into the effluent chambers 94 and 96 to draw off the sludge. A plan view of the sludge draw-off system is shown in FIG. 11 with a cross-sectional view of the system shown in FIG. 12. Sludge traps 130 collect the sludge which is then drawn off by a vacuum pump.

In a similar manner, sludge collects in the anaerobic filters 66 and 68. A similar vacuum draw-off system is used to draw off the sludge. A partical cross-sectional view through an anaerobic filter is shown in FIG. 13. A sludge trap 132 is shown at the bottom where the accumulated sludge can be drawn off by the vacuum system. The baffles of the anaerobic filter and the flow of liquid therethrough can also be seen in the cross-sectional view.

Turning now to details of the A-Tank Complex 46, the A-1 tank 100 is shown in detail in FIGS. 14, 15, 16, and 17 and other Figs. to be identified hereinafter.

Figure 5C:
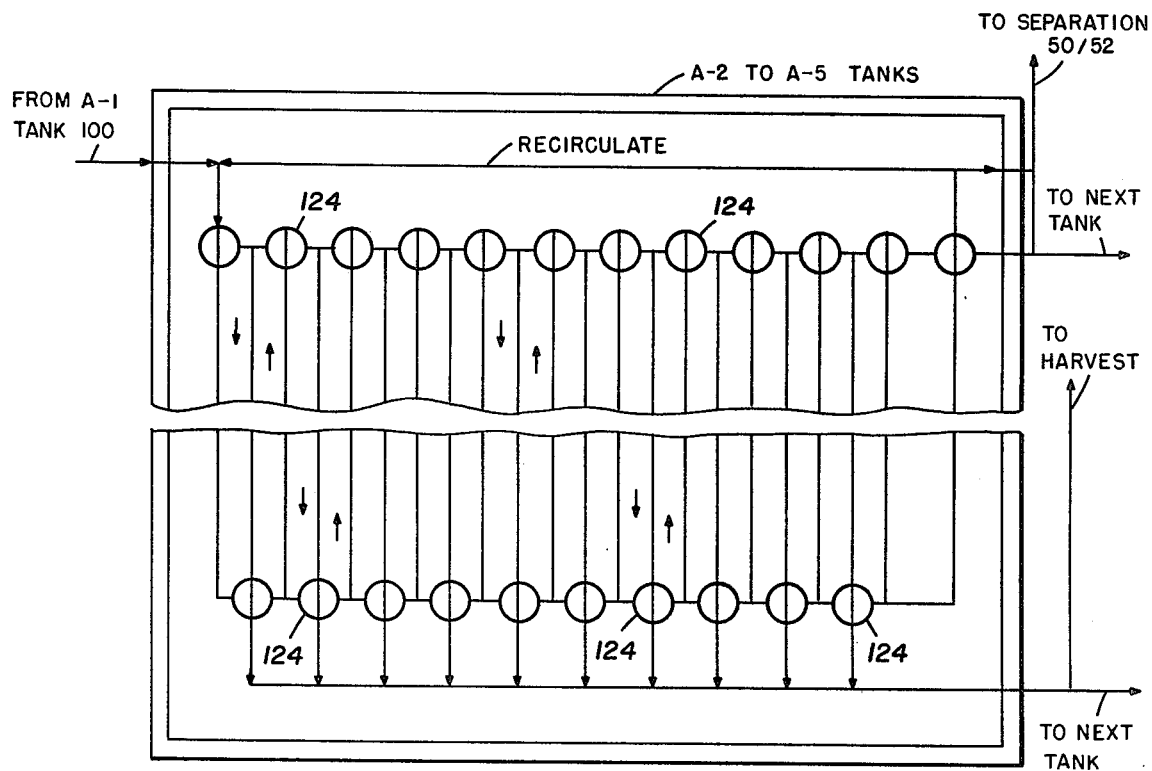
FIG. 5c is a plan view of the A-2 tank showing piping.

In the A-1 tank 100, which is at an approximately level position and situated over (on top of) the B-Tank Complex 44, the effluent flows through the A-1 tank 100 structure in pairs of channels. In FIG. 5, ten of these pairs of channels 134 is shown in schematic format. The pairs of channels 134 are shown beginning and ending in control tanks 124 at each end of each pair of channels 134. It is to be understood that the ten pairs are illustrative for this invention and that any number of channels may be used in accordance with capacity requirements.

An enlarged plan view of a pair of channels 134 of A-1 tank 100 is shown in FIG. 14. As the A-1 tank 100 is situated more or less level on top of the B-Tank Complex 44, some means is needed to cause the liquid to flow through the system. The liquid movement in each of the pair of channels 134 is produced by elevating one end of each channel of the pair of channels 134 so that in one channel 136 the liquid flows in one direction and in the other channel 138 the liquid flows in the opposite direction. Directional lines in FIG. 14 indicate the direction of flow in channel 136 and channel 138. The slope of the channels 136 and 138 can be seen in FIGS. 15 and 16.

The control tanks 124, one at each end of the pair of channels 134 control the flow of the liquid in each of the channels 136 and 138. The control of the liquid flow is handled by pumps with automatic float valve control to keep the flow moving as necessary. One of the pumps 140 can be seen in FIG. 17. One pump 140, as seen in FIG. 17 pumps the liquid from channel 136 over the lowered baffle 142 in the control tank 124 to channel 138. The flow is by gravity to the control tank. At the opposite end a pump 140 pumps the liquid from channel 138 over a baffle 142 to channel 136.

A second embodiment of an A-1 Tank is to use plastics tubes as will be described hereinafter with FIG. 19.

Note how the A-1 tank covers the B-tank Complex 44. The control tanks 124 straddle each side of the B-tank 44 enclosure as the pairs of channels 134 cross over the top of the enclosure.

The culture liquid 48 from the B-Complex 44 is pumped up to the A-1 tank 100 by pump 144 and distributed to the row of control tanks 124.

As algae accumulates and settles in the bottom of the control tanks 124, the algae slurry can be drawn off through the piping system 146 and directed to the harvest system of separation 50 and 52, dewatering 54, and drying 58 to produce algae meal 22. To draw off both sides of the pair of channels 134, the baffle 142 is raised slightly.

Figure 19:
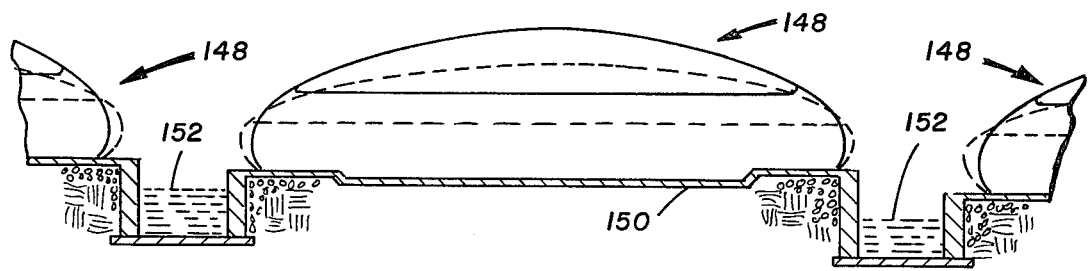
FIG. 19 is a cross section of a plastics tube channel of A-Tanks.

As to the channels, two embodiments are provided in this invention, one is an open channel as shown in FIG. 18 and the other a plastics tube is shown in FIG. 19.

The open channel 138 when placed side by side with a channel 136 forms the pair of channels mentioned hereinbefore. The cross-sectional design shown in FIG. 18 is a typical channel, the configuration could vary, but the capability and use would be the same. The bottom or floor of the channel 138 in FIG. 18 and its companion channel 136, of course are constructed to slope in the direction of flow hereinbefore described. Channels 136 and 138 as a typical pair of channels 134 are used in all of the A-Tanks A-1 tank 100 through A-5 tank 108.

The other channel embodiment is the plastics tube type shown in FIG. 19. A cross section of a typical plastics tube 148 is shown by solid lines when the depth of water in the tube is 12" and in dotted lines when the depth of water is 8". Each tube 148 is carried in a cradle 150, the cradle 150 sloping in the direction of flow as previously described for the open channels 136 and 138. A drain area 152 runs between each channel, this same drain area would also be used between open channels 136 and 138 if space permitted, though such an arrangement is not necessarily required for all arrangements.

Referring again to FIG. 14, note the lip edge 154 at each end of the channels 136 and 138. The lip edge 154 mates with the open channels 136 and 138, or when the plastics tube channel 148 is used the lip edge 154 mates with the tube channel 148. In the case of the open channels 136 and 138 a special transition piece connects the open channels 136 and 138 to the control tanks 124. In the case of the plastics tube channel 148 a special tube-like transition piece connects the tube channel 148 to the control tanks 124. Plastics tubes are transparent.

In the A-Tank Complex 46, A-tanks A-2, A-3, A-4, and A-5 are alike. The A-2 tank 102 will be described as typical of all the aforementioned A-2 through A-5 tanks.

Figure 20:
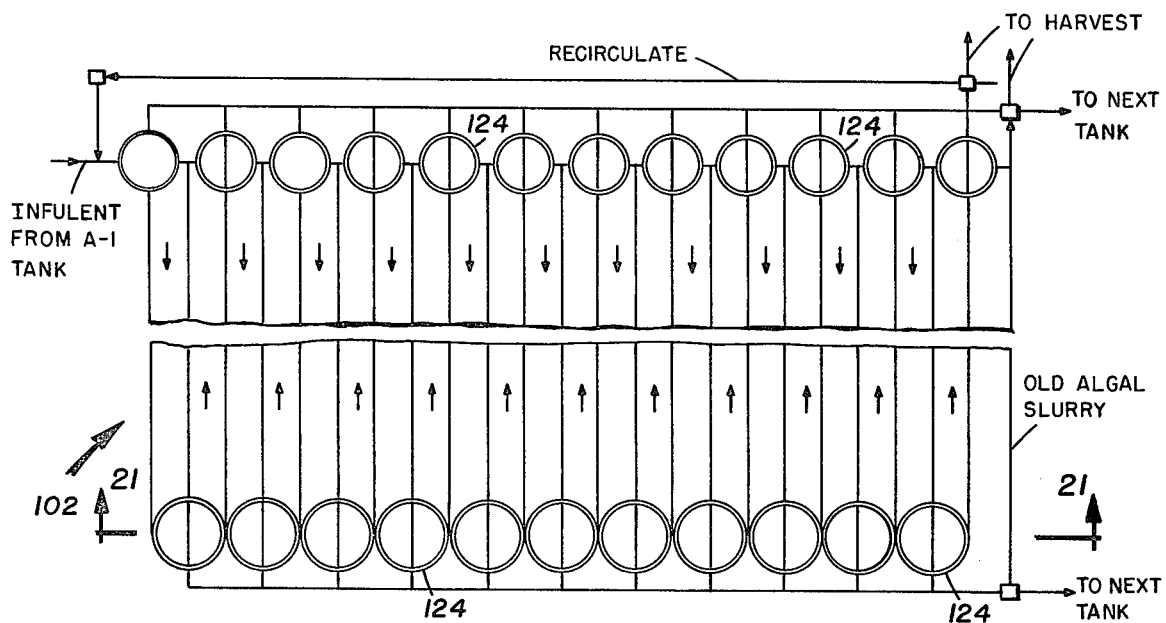
FIG. 20 is a plan view of an A-2 Tank.
Figure 21:
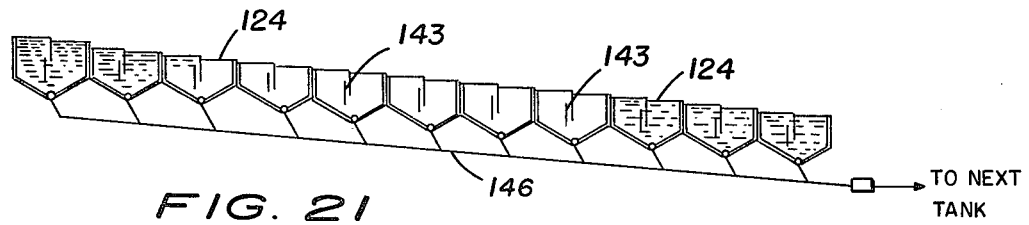
FIG. 21 is a cross sectional view on line 21—21 of FIG. 20.
Figure 22:
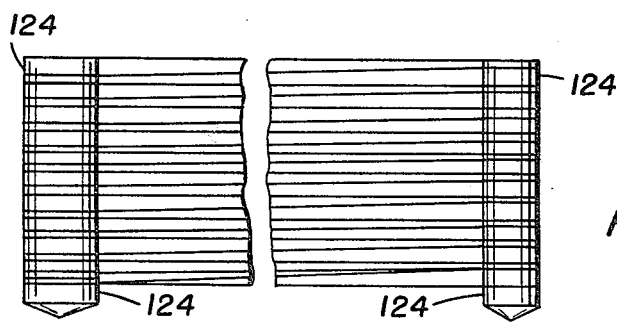
FIG. 22 is an end view of FIG. 20.

FIG. 20 is a plan view of the A-2 tank 102 and FIG. 21 is a cross sectional view through the control tanks 124. In the case of the A-Tanks A-2 through A-5 when set on a hillside, the flow of liquid through the tanks is by gravity. However, if a hillside or an artificial incline is not available, a system of pump units in the control tanks, as used in the A-1 tanks 100, would be necessary. FIG. 22 is an end view of FIG. 20.

As in the arrangement of the A-1 tank 100, drawoff pipes remove settled algae and transport it to the aforementioned part of the system for harvest. Valves in the piping system permit closing off the various elements of the tank segment for repairs and maintenance.

The daily amount of solar energy that reaches the earth's surface is a function of astronomical, geographical, and meteorological phenomena which produce wide daily and seasonal variations.

The solar flux available for photosynthesis in the controlled natural purification system of this invention will vary daily and seasonally as noted hereinbefore.

Another aspect of the operation of the controlled natural purification system is that if left in a more or less static state, the waters in the system would reach a condition where the aforementioned solar energy would reach only a limited portion of the cells in the system. Moreover, during periods of moderate to high intensity radiation, light saturation and supersaturation occur which seriously inhibit algal growth. Exposing algal cells intermittently to extremely short periods of light and darkness partially overcomes the problems of light saturation and of a portion of the cells being shielded from exposure to sufficient light.

To overcome the problems mentioned hereinbefore, two procedures are included in the present invention: the addition of controlled artificial light; and the introduction of turbulence.

As has been noted hereinbefore, the constant light intensity related pumping, aided by gravitational flow in the moving of the liquid biomass back and forth through the system of control tanks, channels, tubes, and other means during periods of moderate to high insolation provides turbulence to significantly increase the efficiency of light energy conversion to photosynthate, algal growth and yield. Further turbulence is provided in the A-6 tanks that will be described hereinafter.

The introduction of supplemental pulsed lighting is an important aspect of this invention. FIG. 23 illustrates the addition of supplemental light facilities 156 to the control tank end of an A-2 tank 102. It is to be noted that the illustration of a supplemental light facility 156 to an A-2 tank 102 is also applicable to any of the segments of the system if found desirable or necessary to improve the growth and recovery of algae. Thus, such supplemental light facilities 156 may be added at selected control tanks 124 or at each and every control tank 124 in the overall system, and can be added to the A-1 tank 100 segment, the A-3 tank 104 segment, the A-4 tank 106 segment, and the A-5 tank 108 segment as required or selected for the system. A supplemental light facility similar in elements, but different in application, may also be added to the A-6 tank 110 segment.

The supplemental light facilities 156 attached to the control tank 124 consists of an end light tank 158, a plurality of lower baffles 160, a plurality of upper baffles 162, and a plurality of light clusters 164.

The liquid in the control tank 124 instead of being pumped over the baffle 142, as hereinbefore described, is pumped over the rim of the control tank into the end light tank 158. The liquid then flows over the lower baffles 160 and under the upper baffles 162 as it flows around the end light tank 158. At the end of this flow through the end light tank 158 it flows into the control tank 124 over the short side of the control tank 124 and thence into the plastics tube 148. Directional arrows in FIG. 23 indicate the direction of flow. As the liquid flows alternately over lower baffles 160 and under upper baffles 162 it concurrently flows around the light clusters 164 which are described hereinafter.

The flow of the liquid can be shunted so as to bypass the end light tank 158 by pumping over the baffle 142, or by raising baffle 142 and depending on gravitational flow if in A-2, 3, 4, or 5 tanks or if in A-1 tank on the pump on the conrol tank 124 at the opposite end to keep the liquid flowing. In the bypass the short side of control tank 124 adjacent to the end light tank 158 must be closed off, either by closing the short side or by closing off the flow through the adjacent upper baffle 162.

The flow over lower baffles 160 and under upper baffles 162 can be seen clearly in FIGS. 24 and 25.

Regarding the light clusters 164, FIGS. 26 and 27 illustrate the details. The light cluster 164 consists of a top frame 166, a bottom frame 168, a water-tight enclosure 170, a plurality of fluorescent lamps 172, a center-light reflector 174 with a plurality of surfaces to match the plurality of surrounding fluorescent lamps 172, and a centering base 178.

The bottom frame 168 has a centering node 176 to fit and center in the centering base 178 which is attached to the bottom of the end light tank 158. Means to lower the light clusters 164 into position and to steady them in place is not shown. Such means for lowering and steadying permit removal of the light clusters 164 for repairs and maintenance. All wiring to the water-tight enclosure 170 is waterproof and is either enclosed in the central core or is installed above the water level. The water-tight enclosure 170 is transparent for the transfer of light to the liquid.

It is to be understood that a light cluster 164 with fluorescent lamps set horizontally or at any other angle other than vertical as illustrated is within the scope and intent of this invention.

The light cluster 164 may be automated for short or long periods of lighting or may be timed and controlled for light pulses of 3 to 30 milliseconds on and off or any other duty cycle determined. Experimentation will determine the best timing and the period when such artificial light is to be used to obtain the greatest cost effective yield of algae growth.

When senescent cells precipitate in the control tanks 124 and in the A-6 tanks 110 (as described hereinafter), the settled algae units will be drawn off and harvested separately. Such heavier and less metabolic cells interfere with the younger, faster-growing, cells by producing toxic substances, by masking light, and in other ways. The separate harvesting eliminates this problem.

Turning now to the A-6 tanks 110, there are several modes in which the A-6 tanks 110 may be arranged, connected, and operated in conjunction with the other A-tanks in the A-Tank Complex 46.

The arrangement, connection, and operation can be tailored to fit the requirements at hand for treating wastewater of varying volumes and for recycling the treated water for algae farming. In reality, there is no limit as to the volume that can be treated if space is available for the arrangement of the system. As hereinbefore described, in addition to a B-Tank Complex 44, the A-Tank Complex 46 may be any combination of the A-Tank Complex 46 system: A-1 tank 100; A-2 tank 102; A-3 tank 104; A-4 tank 106; A-5 tank 108; and A-6 tank 110.

The A-1 tank is always placed over the B-Tank Complex 44 as hereinbefore described and the controlled natural purification system could be sufficient at that point for a small volume of wastewater.

As the volume increases, additional segments of the other A-tanks (A-2 tank 102 through A-6 tank 110) may be added in accordance with the volume of wastewater to be handled. These additional segments may be in any combination, if space is available, and installed in the various modes as hereinbefore described for the A-2 tank 102 through A-5 tank 108 and for the A-6 tank 110 as hereinafter described.

It is also to be noted that for extremely large volumes of wastewater that parallel systems of more than one B-Tank Complex 44 with an A-1 tank 100 over each and additional combined A-tanks in the A-Tank Complex 46 could be installed, again space being available. Such expansion of the system is within the scope and intent of this invention.

The harvesting of algae for algae meal 22, as hereinbefore described is a part of the present invention. Points of harvesting have already been described for the A-tanks A-1 through A-5 and the harvesting from A-6 tanks 110 will be described hereinafter.

In all of the algae harvesting, the slurry is piped to the concentration points 50 and 52, the dewatering point 54 and the drying 58 as hereinbefore described to produce the algae meal 22.

An A-6 tank 110 is shown in enlarged plan view in FIG. 28. The direction of flow of the wastewater being treated is shown by the directional arrows. As can be seen from FIG. 28 the A-6 tank 110 is more or less shaped like an "8", it may be said to be somewhat guitar-shaped. A longitudinal center island structure 180 divides the flow of the liquid passing through the A-6 tank 110. Details of the center island structure 180 will be described hereinafter.

In addition to the center island structure 180 dividing the flow of liquid, directional flow vane structures 182 guide the flow of liquid around the ends of the A-6 tank 110 and prevent short circuiting of the flow to help maintain a homogenous cell concentration.

A mixer impeller 184 provides a means for inducing turbulence and mixing the partially treated wastewater which is now a culture liquid. The mixer impeller is shown at one end only, but it is to be understood that such a mixer impeller may be placed at the corresponding opposite end also, and others may be placed at other locations when additional turbulence is required or found to be desirable to promote the growth of algae.

The influent of partially treated wastewater is brought in by piping at influent entrance 186 and discharged into the flow of liquid in the A-6 tank 110 at the discharge nozzle array 188 across the width of the flowing stream.

As the algae grows in the flowing stream, moving around the A-6 tank 110, the older heavier algae is collected in sedimentation tanks 190, built into the bottom of the A-6 tank 110 structure. One of these sedimentation tanks can be seen in cross section in FIG. 29. The precipitated or senescent algae is harvested from the sedimentation tanks 190 by chain-driven scrapers 196 extending into the tank and then pumped as a slurry to the aforementioned dewatering point 54 and drying site 58 as hereinbefore described.

The speed of the flow in the A-6 tank 110 varies and is dependent upon several factors. The variation in speed also provides turbulence at some points and a quieter flow at other points. The rate of input at the influent entrance 186, the rate of output at the effluent discharge point 192, the timing and rate of removal of algae slurry at the sedimentation tank 190, the change of velocity of the liquid by the flume effect at the waist of the A-6 tank 110, and the rate of recirculation through recirculation channels 194, all provide variations in the speed of the flow of the liquid in the A-6 tank 110.

Depending upon whether the A-6 tank 110 concerned is the first such tank in a group, the last such tank in a group, or the only such tank in a complex, the effluent discharge 192 may be piped 210 to the next A-6 tank 110 in the group, or piped to a point for further separation of algae and then discharged as treated reclaimable water 60.

At the down-stream side of the sedimentation tanks 190 the floor of the A-6 tank 110 has a slightly higher elevation than the upstream side, usually several inches. A rise in the side 198 of the sedimentation tanks 190 provides this slightly higher floor elevation of the A-6 tank 110. The floor again drops down to the normal elevation at the drop point 200. The rise in the floor at the down-stream side 198 of the sedimentation tank 190 and the pressure build-up before the velocity increases at the waist due to the Bernoulli effect facilitates settling of older, heavier algae. The flow is slowed over the in-line sedimentation tanks 190 so that a significant amount of this algae precipitates and settles in the sedimentation tanks 190 on each passing.

Where the influent for the A-6 tank 110 may be received from another A-6 tank 110 if they are in an operating complex together, the influent entrance 202 may be used instead of or in conjunction with the influent entrance 186.

Influent that flows in through influent entrance 202 is discharged into the stream through a discharge nozzle array 204 as previously described for the discharge nozzle array 188.

A walkway for servicing and maintenance is provided at the top of the center island structure 180 with suitable means to reach the walkway.

The aforementioned recirculation channels 194 provide for recirculating a portion of the fluid in each of the end nodes of the figure "8" shaped A-6 tank 110. In addition, a portion of the liquid shunted off for recirculation at each end is further shunted through a pumping system 206 for discharge through the discharge nozzle array 204 and through a nozzle array 208.

The biochemical oxygen demand reduction is completed in the sunlighted A-Tank Complex 46 in an $O_2$-$CO_2$ symbiotic exchange with algae. The algae photosynthetically metabolize the bacteria-converted nutrients in the $CO_2$-enriched culture liquid. Supplemental $CO_2$, diffused throughout the biomass in a five percent mixture in air, is a by-product of aerobic decomposition, and of combustion of hydrocarbon fuels used in the algae drying, including process-produced methane.

In FIG. 28 the introduction of the air-$CO_2$ mixture is at the center island 180 area. The $CO_2$ from the aforementioned points in the controlled natural purification system 10 is piped into the system at the $CO_2$ entrance 212 for introduction at the gas diffusion chambers 284. The piping arrangement is shown in subsequent figures of the drawings.

As biologically-effective light is the limiting factor in the A-Tank Complex 46, all other variables are aligned to produce maximum algae yield and high effluent quality. After algae removal and disinfecting the effluent, it meets advanced treatment standards. In this final stage of the process 95% of the algae are separated, concentrated, dewatered, and dried for marketing as hereinbefore described.

In this A-Tank Complex 46, where possible the A-tanks 100 through 110 should have the maximum of southern exposure for the maximum year-round insolation. The A-1 tank 100 through the A-5 tank 108 are discrete enclosed environments when comprised of the plastics tubes 148 which provide high light-transmissivity with the control tanks 124 through which the culture liquid 48 flows. In the pair of open channels 134, instead of the plastics tubes 148, the difference is that the environment is not enclosed. The other photosynthetic unit, the A-6 tank 110 is a more or less shallow open vessel at grade level for storage and final polishing treatment before the major algal harvest.

In the A-2 tank 102 through the A-5 tank 108, which are set in a sloped array, the flow is by gravity in a more or less zig-zag fashion through the various channels. The control tanks can be arranged, and automated if necessary, to slow or accelerate the flow of liquid or to stop it entirely, in coordination with any varying light intensity. These tanks are equipped for draw-off of senescent algae that inhibit further growth. The difference in the A-1 tanks 100 is that the liquid circulates back and forth in a pair of channels until otherwise directed elsewhere. The A-1 tanks 100 can be used for culturing faster-growing strains of green and blue-green algae for seeding the other photosynthetic tanks aforementioned.

In this entire process the flow of the liquid in the A-1 tank 100 through the A-5 tank 108, and the intermittent recirculation in the various tanks, gives maximum exposure to the sun, while the mechanical mixing and controlled gravity flow resuspends precipitated solids and gives controlled intermittent cell exposure to intense sunlight.

An alternative method for providing additional turbulence in the flow through the A-2 tank 102 through the A-5 tank 108, is to provide baffle-like tubes or rods, not shown or numbered, at spaced distances under the plastic tubes 148 and at alternating inclined angles to jostle the light from side to side and up and down as it passes through the plastic tubes 148.

An advantage of the plastics tubes 148 over the open channels 134 is that there are no side walls to shade a portion of the liquid when the solar rays are from one side or the other, thus providing greater exposure to the solar rays.

Another advantage of the plastics tube 148 is that in winter, when slower growth conditions require lower cell densities and depths, the depth of the water in the plastics tubes 148 can be reduced. This lower depth flattens out the plastics tube 148 and so increases the photosynthetic capacity for solar radiation.

The baffles 143 in the control tanks 124 in the A-2 tank 102 through the A-5 tank 108 control the gravity flow through the line of sloped tanks. When the influent rate (correlated with the light intensity) is low the baffles are lowered to slow the passage (when the baffle 143 is completely down the liquid is quiescent). The lower part of the baffle 143 in FIG. 21 is shown raised so that the liquid can flow, by gravity, through the series of control tanks 124 and the connected plastics tubes 148 (or open channels 134) as indicated by directional arrows in FIG. 20.

The control tanks 124 have removable transparent covers (not shown or numbered) which help to control seasonal culture temperatures. Removal of the covers in the summer permits heat loss by free evaporation. Additional heat loss can be achieved by routing a portion of the culture liquid through heat exchanger in the aerated B-1 tanks and B-2 tanks 70 and 71. Covering the control tanks 124 in the winter help to retain heat in the culture.

It is to be noted that the aforementioned introduction of an air-$CO_2$ mixture into the A-6 tank 110 may also be introduced into the liquid in any of the A-tanks A-1 tank 100 through A-5 tank 108.

Biomass control, the process of removing settleable algae and other settleable materials from the A-Tanks, has been described hereinbefore regarding the removal of algae for harvesting. Settling and then resuspension by mixing of older algae have a detrimental effect on biomass growth. The older cells compete for light and nutrients and they may produce an autoinhibitory substance which impedes or completely blocks reproduction. Another detrimental effect of biomass growth is that suspended inorganic precipitates may substantially reduce light penetration into the cultures.

The settleable algae and other settleable materials tend to precipitate when the biomass is quiescent or moving very slowly, notably from late afternoon to midnight. In the present invention these precipitates are accumulated for removal for harvesting in the hopper bottoms of the control tanks 124 and the sedimentation tanks 190.

A second embodiment of an A-6 tank 110 is shown in FIG. 30, with a cross-sectional view shown in FIG. 31. The second embodiment of A-6 Tank 110 might be referred to as a draw-down and refill chambers structure. The details are described hereinafter.

The second embodiment of the A-6 tank 110 has features similar to the first embodiment and in FIG. 30 these are given similar numbers. Such similar features are the more or less figure "8" shape or guitar-shaped configuration, a center island 180, directional flow vane structures 182, mixer impellers 184 at each end, influent entrance 186 from the B-Tank Complex 44, a discharge nozzle array 188 for the influent from influent entrance 186, influent entrance 202 from next A-6 tank, effluent discharge 192, recirculation channels 194 (these recirculation channels 194, like those in the first embodiment, recirculate a portion of the liquid within the node at one end or the other of the figure "8" configuration), a nozzle array 204 for dispersing the influent from the influent entrance 202, pumping systems 206, and a nozzle array 208. Operation of the aforementioned similar features of both first and second embodiment of the A-6 tank 110 operate in exactly the same manner. The air-$CO_2$ introduction and diffusion is the same in both embodiments.

The drawn-down and refill operation for the second embodiment of the A-6 tank 110 is described hereinafter.

In FIG. 30, five draw-down and refill chambers 214 are shown around the periphery of the A-Tank 110. It is to be noted that three draw-down and refill chambers 214 are at one end, only two at the opposite end. This is because at the end where there are only two draw-down and refill chambers 214 there is also a draw-down chamber 216 at the effluent chamber 192. In addition, there are two small sedimentation chambers 218, one in each node of the A-6 tank 110.

Settled algae in the draw-down and refill chamber 214, the draw-down chamber 216, and the sedimentation chambers 218, are harvested by vacuum removal. To facilitate the accumulation of algae at these points floor sweeping is used. The piping lines 220 have a three way use, draw-down to remove the liquid except for the last inch or less in the A-6 tank 110, vacuum removal of the algae slurry brought to the eight points of removal, and refill of the A-6 tank 110 after the algae is removed.

It is to be noted that vacuum removal of algae from the draw-down and refill chambers 214, the draw-down chamber 216, and the sedimentation chambers 218 may be made without a complete draw-down of the A-6 tank 110 and subsequent refill. The draw-down and refill is only performed when the algae is to be swept to these points, accumulated, and then harvested for the entire A-6 tank 110 floor.

When there are a group of A-6 tanks 110 in the system (either in series, in parallel, or a combination of both) the draw-down and refill operation is as follows. Draw-down the first A-6 tank 110 from an approximate depth of 12 inches to a depth of one inch or less, the liquid removed is transferred to several other A-6 tanks 110 so as to increase their depth from approximately 12 inches to approximately 15 inches (depending on how many A-6 tanks 110 are in the cluster). Sweep the algae in the one inch algae slurry on the A-6 tank floor to the draw-down and refill chambers 214, the draw-down chamber 216, and the sedimentation chamber 218, and remove the algae through the draw-down system. Then refill the A-6 tank 110 from the next A-6 tank 110 and proceed as before to remove the algae.

It is to be understood that direct vacuum removal of the algae from the floor of the A-6 tank 110 through a vacuum system that separates the algae for harvest and returns the water to the A-6 tank 110 is within the scope and intent of this invention.

Liquid required to bring all A-6 tanks 110 in the cluster back to the normal depth after the loss of a portion during the removal of algae will be reconstituted from liquid from the A-tanks in the system before the A-6 tank 110 components.

Some natural sedimentation will occur in the sedimentation chambers 218, in the draw-down chamber 216, and in the draw-down and refill chambers 214 by the regular flow of the liquid. These chambers receive settling senescent algae when the culture liquid is quiescent or moving slowly. Such settled algae may be removed periodically without resorting to the draw-down and refill procedure. The sedimentation chambers 218 are approximately two feet deep and are positioned to take advantage of backwater conditions when the liquid is moving slowly. The other chambers are also approximately two feet deep.

Figure 32:
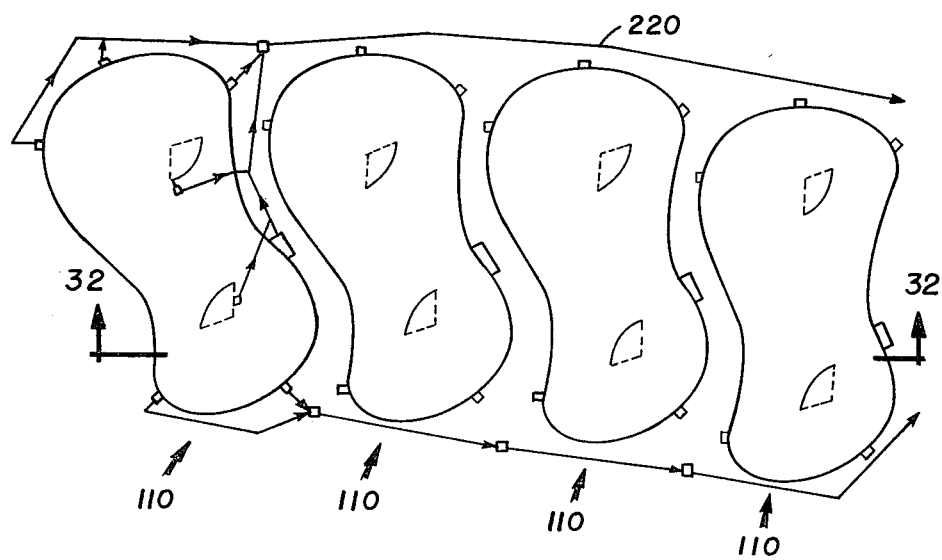
FIG. 32 is a plan view of a group of A-6 Tanks of the second embodiment.
Figure 33:
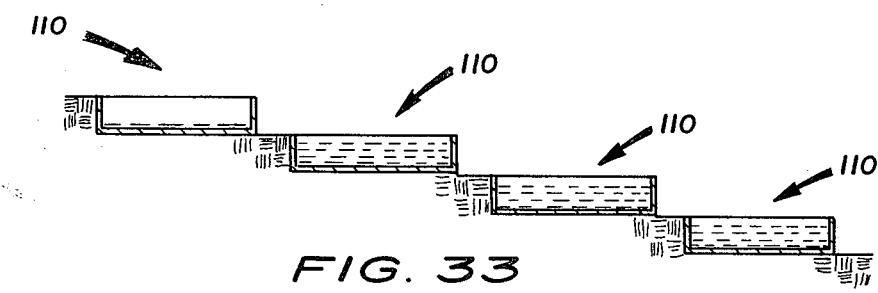
FIG. 33 is a cross sectional view on line 33—33 of FIG. 32.

Hereinbefore it has been pointed out that the A-2 tank 102 through the A-5 tank 108 are best operated when on a slight incline or hillside as shown in FIG. 6. Also in that same FIG. 6 the A-6 tank 110 is shown level at grade. It is to be understood that the A-6 tank 110, when in a group arrangement, may also be set on a hillside or slight incline. This is particularly true when the A-6 tank 110 is used as in the second embodiment, the draw-down and refill system. FIGS. 32 and 33 illustrate a group of A-6 tanks on an incline, with the uppermost A-6 tank shown with the liquid level drawn-down as hereinbefore described. Only the uppermost tank has the piping shown for removal of algae, however, all tanks would be connected to the piping in a similar manner.

Figure 34:
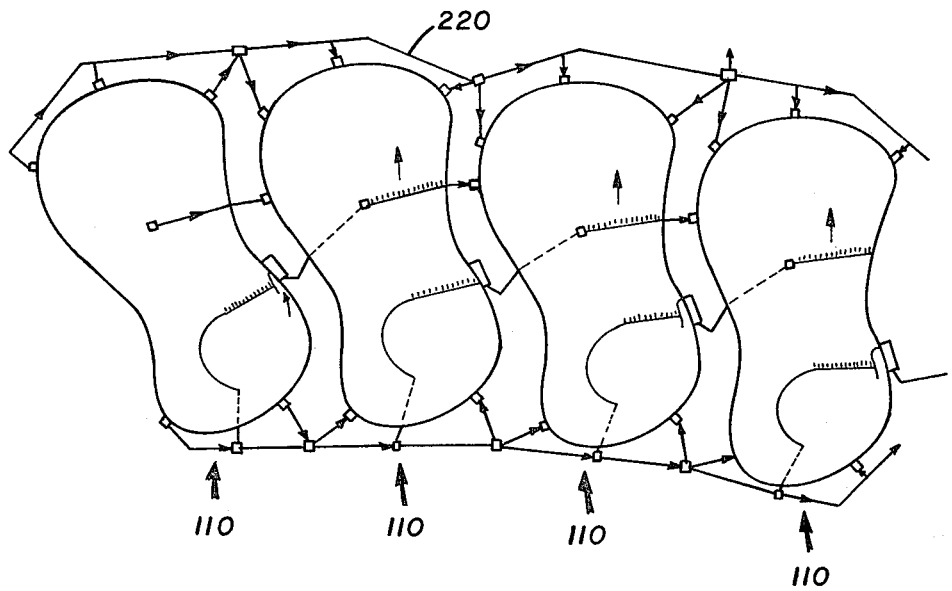
FIG. 34 is a plan view of a group of A-6 Tanks of second embodiment showing piping for the draw-down of one tank.

In FIG. 34 a group of A-6 tanks are shown with piping for the draw-down of the first tank. It is to be noted that if the A-6 tanks are not set on an incline or hillside to provide gravity flow, then a pumping means is required.

Figure 35:
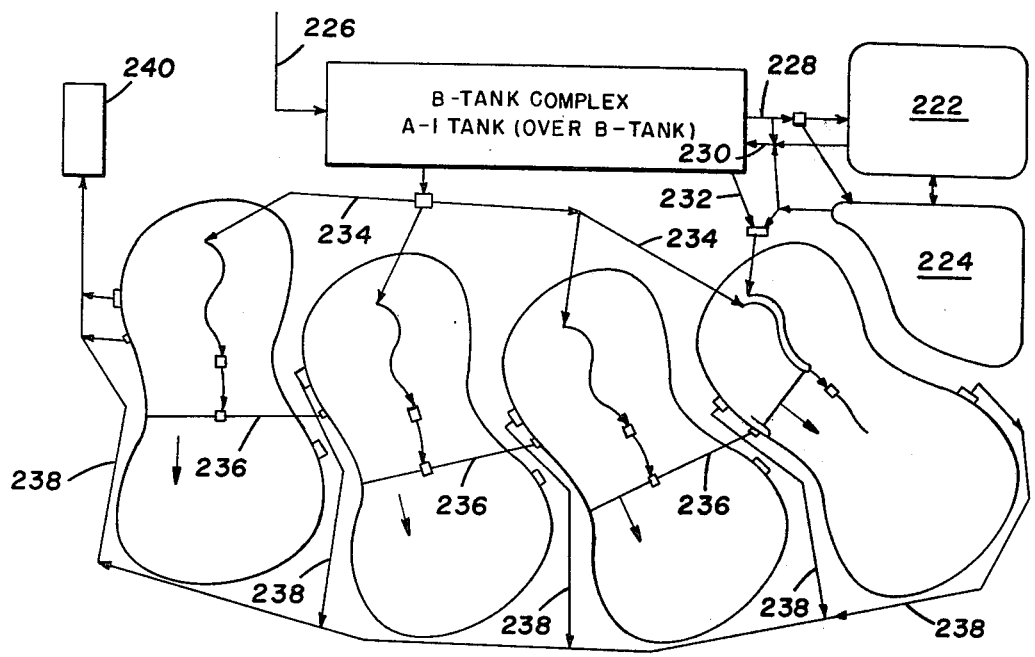
FIG. 35 is an array of A-6 Tanks connected in series.
Figure 36:
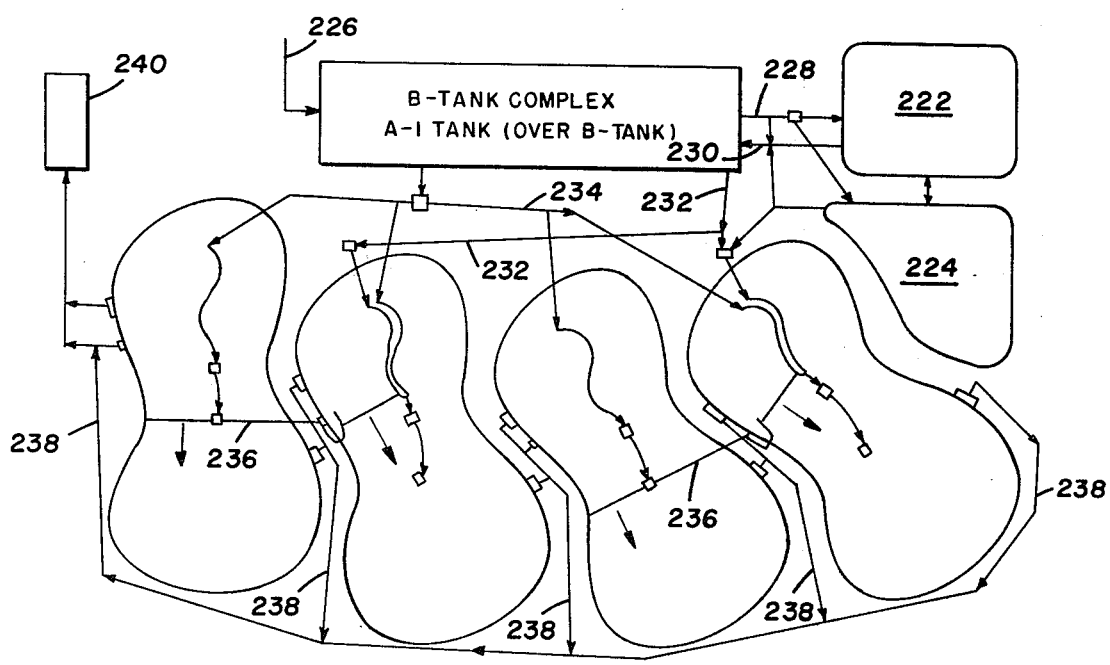
FIG. 36 is an array of A-6 Tanks with pairs of tanks connected in series and the series connected in parallel.

As hereinbefore indicated, the A-6 tanks 110 may be connected in series, in parallel, or a combination of the two. FIG. 35 shows an array of A-6 tanks connected in series. FIG. 36 shows an array of A-6 tanks first connected as a pair of A-6 tanks in series and then the two series of A-6 tanks are connected in parallel.

In FIGS. 35 and 36 it will be noted that two ponds are shown in the arrangement. The first pond 222 is for winter storage of B-Tank treated liquid which can be a reserve supply or a holding pond while portions of the A-Tank Complex 46 are cleared. The second pond 224 is used the same as the first pond. While these ponds 222 and 224 are not required for all controlled natural purification systems 10, the use of ponds 222 and 224 is shown for those large systems that may need the extra capacity.

The piping shown schematically in FIGS. 35 and 36 are substantially the same as far as conducting liquid from point to point. The only difference is the fact that the arrangement in FIG. 35 connects the tanks in a series arrangement and in FIG. 36 after each pair of tanks are connected in series the pairs of tanks are then connected in parallel in the system.

Figure 37:
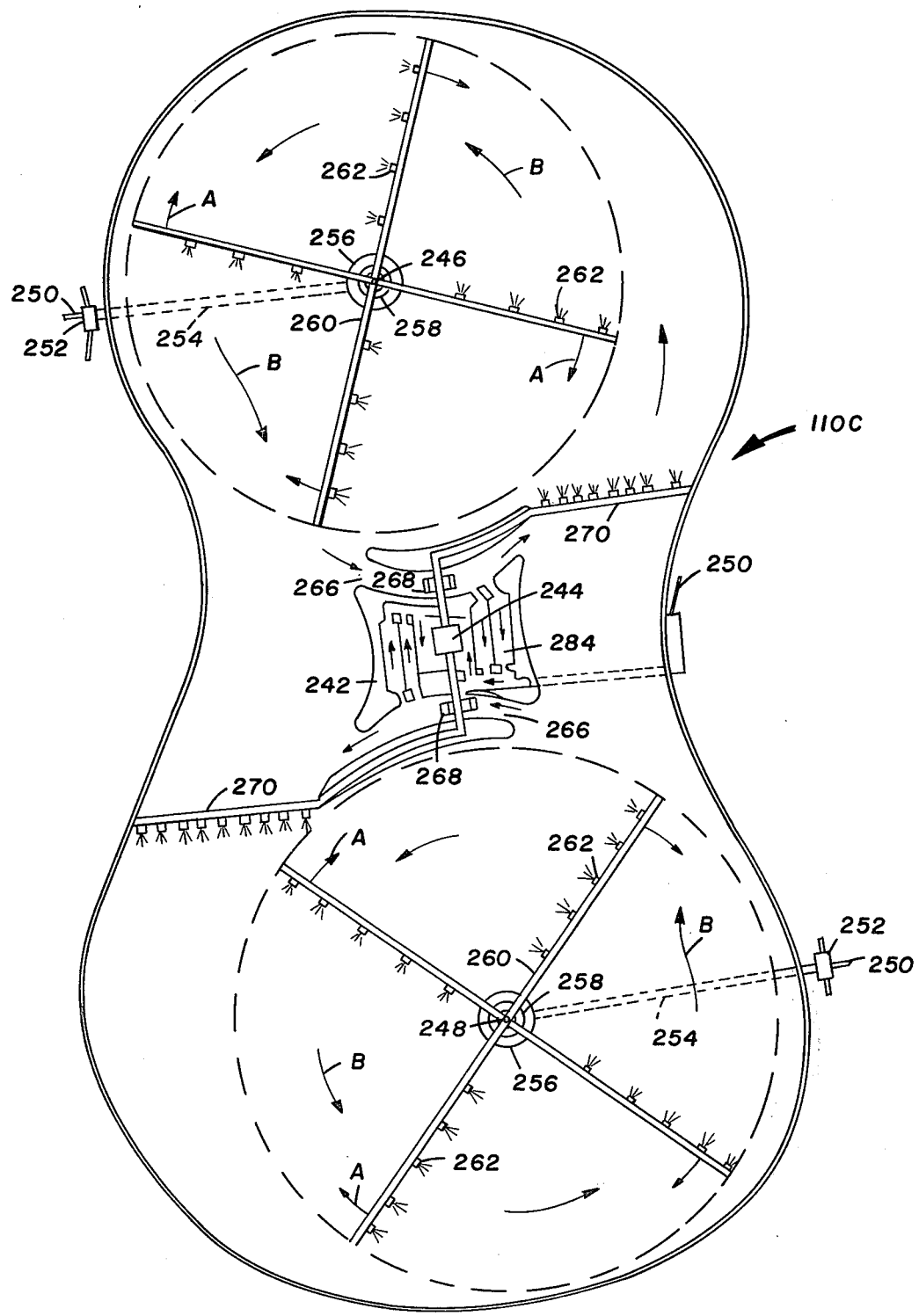
FIG. 37 is a third embodiment of an A-6 Tank.

A third embodiment for an A-6 tank is shown in FIG. 37. The tank exterior configuration is essentially the same as the first and second embodiments, the difference being in the shape of the center island 242 and the handling of the movement of the fluids.

The third embodiment has a shallow depth, typically in the vicinity of eighteen inches. It is designed for high-rate algal growth and efficient separation of the algae from the water (primary concentration) by a drawdown procedure, a vacuum sweep to harvest the algae, and then a refill for the next operation.

The third embodiment comprises the two nodes of the figure 8 shaped tank, and it should be understood that these nodes may be the same size and shape or one may be larger than the other. Such a variation is within the scope and intent of this invention. The center island 242 as noted hereinbefore is a slightly different shape than the first and second embodiments, for gas diffusion ($CO_2$ enrichment). In this third embodiment the recirculation and primary influent distribution is powered by a pump 244 and rotating distributor 246 and 248. This system for recirculation and primary influent distribution induces controlled inter- and intra-nodal flows.

The distribution systems in each nodal area also contribute to the aforementioned inter- and intra-nodal flow.

The aforementioned combined controlled daytime flows provide a homogeneous mixing of the culture liquid, eliminating short-circuiting and the thermal stratification. During hours of high solar intensity, mixing is accelerated to briefly expose to light as many cells as cost-effectively possible. Conversely, when the radiation is low, the flow rate is correspondingly low and close to nil. The nodal distribution system provides the means for primary algae concentration by precipitation, drawdown, and vacuum sweep; and also for refill.

To differenciate between the three embodiments of the A-6 tank 110, the first embodiment in FIG. 28 is designated 110A, the second embodiment in FIG. 30 is designated 110B, and the third embodiment is designated 110C.

The distribution system for the incoming primary influent 250, at pump 252, is through a piping system 254. The piping system 254 is so arranged for multi-purpose use, it serves for input of primary influent, drawdown, algae harvest, and tank refill.

In each node the distribution system is the same. The piping system 254 connects to an automated circular weir 256, then to a rotating manifold 258 on a central column of horizontal waterwheel 248, an then to the combined water distributor and vacuum inlet units 260.

The rotating manifold 258 has two or more arms 260 attached to the central supply and support column. These rotating manifolds and arms are similar to the rotating manifolds and arms of trickling filters.

A plurality of vertical pipes descend from the arms 260 and from these vertical pipes are distributing heads 262. The plurality of distributing heads 262 are in the culture liquid at varying depths (the vertical pipes, none shown or numbered) extend downward into the culture liquid to give the distributing heads 262 their varying elevations in the culture liquid.

Also connected to the vertical pipes of one of the arms 260 are distributor-vacuum intake units (not shown or numbered) which are also positioned in the culture liquid at varying depths. The manner in which the distributing heads 262 and the distributor-vacuum intake units operate is described hereinafter.

All arms 260 distribute liquid received from pump 252 through the piping system 254 and the rotating manifold 258. The liquid from the arms 260 flows down the aforementioned vertical pipes or legs (not shown or numbered in FIG. 37) and then out through the distributing heads 262. The jet action of the liquid squirting from the distributor heads 262, while immersed in the culture liquid, drives the arms 260 forward in a circular motion around the center of the waterwheel 248 by way of the physical connection of the distributor heads 262 to the vertical pipes or legs (not shown or numbered) which are connected to the arms 260. At the same time, the culture liquid in the A-6 tank 110C at this node location is forced into a circular motion the reverse of the movement of the arms 260. The directional arrows "A" indicate the direction of circular movement of the arms 260, and the directional arrows "B" indicate the direction of circular flow of the culture liquid.

As noted hereinbefore, one of the arms 260 also serves as the base for the distributor-vacuum intake units. When this arm is in operation for the distributor-vacuum intake units the other arms 260 are closed or blocked off. When the algae are ready to be harvested, the water is drawn down, somewhat slowly by lowering the circuit weir 256 very slowly to draw off the liquid, similar to the previously described drawdown of an A-6 tank 110, except that in this embodiment the drawdown is through the circular weir 256. When the liquid is down to a more or less algae slurry consistency, the draw-down ceases. At this point a distributor-vacuum intake unit (not shown and not numbered) is attached to each of the distributor heads 262. A vacuum sweep machine is connected to each said distributor-vacuum intake unit one such connection at a time). As the vacuum sweep machine moves forward, sweeping a circular path or swath around the nodal area, the vacuum of the system sucks in the algae slurry and thence through the distributor-vacuum intake unit and thereby through the system to the final algae drying as hereinbefore described. Then, in turn, the vacuum sweep machine is connected to each of the other distributor-vacuum intake units, and in turn, another path around the nodal area is made to suck in the algae slurry. A slight slope toward the weir 256 facilitates the process.

The connection of the arms 260 to a central supply and support column is similar to rotating manifolds and arms of trickling filters. Where the jet action of the liquid squirting from the distributor heads 262 is insufficient to propel the arms 260 an electrical motor on the central column is provided to assist the movement.

In the aforementioned vacuum sweep of the floor of the A-6 tank 110 nodal area, the arms 260 are pushed forwardly by the movement forward of the vacuum sweep machine pushing against the flexible connection to the distributor-vacuum intake unit. Other areas of the A-6 tank 110 outside the nodal areas are swept clean of algae slurry by the same vacuum sweep machine which is connected to the nearest distributor-vacuum intake unit (in either node) by a flexible hose.

As noted hereinbefore, the rotating manifold 258 is similar to those used in trickling filters, however, with the following exceptions: the dual use of one arm for influent distributor and vacuum removal of algal slurry; and the extension into the culture liquid of the distributor outlet (the distributor head 262) and the parallel location of the distributor-vacuum intake units, not only for the functions mentioned, but also for jet action to provide partial or complete manifold propulsion. The latter action provides liquid flow rates at near-optimum cost-effective mixing conditions.

The control units for the third embodiment of the A-6 tank 110, one in each node, operate in consort from a remote point. The control units, centered around a central column 290, may be a plastics material. They are circular tank-like devices and are equipped with circular weirs or dams 256 that move up and down, such as when used in a draw-down operation, or when refilling the tank, or for recirculation.

When the circular weir 256 is up, the liquid culture 48 is contained in the A-6 tank 110 at operating depth. Gradual lowering of the weirs during draw-down permit a decanting of surface water free of precipitating algae, thus discharging treated, final effluent and expediting primary concentration of the algae for harvest on the tank floor 292. During refill the process is reversed and the influent flows over the circular weirs 256 into the A-6 tank 110, as the weirs are gradually raised to operating tank-water depth.

Recirculation of the culture liquid is accomplished by lowering the circular weir 256 to allow tank water to overflow 294 into the circular cup-like decanter 296 at the interior lip of the weir 256. The decanted liquid is discharged via flexible supply pipes 298 to one or more hydraulic rams or lift pumps 314, and sump pumps 300 to be pumped up the central column 290 into the rotating manifold 258 for redistribution into the A-6 tank 110. Tank water decanted into the weir cup provides pressure and velocity heads to recirculation and effluent streams. Sump water accumulated in recirculation, including water rejected by the hydraulic rams and water overflowing the weir cups, is pumped up the central columns for redistribution, by sump pumps. Recirculation is also achieved inter- and intra-nodally by forces previously described at the center island.

In the piping system 254, two dual-purpose pipes under the tank connect pump 252 and automated valves at the perimeter. One is the influent-algae slurry discharge line 310 and the other, a larger-diameter pipe, is the influent-effluent line 312. The control unit, essentially an uncovered tank, constitutes the influent-effluent chamber for recirculation of the tank liquid up the central column, draw-down and then out the influent-effluent pipe, or refill after vacuum sweep by reversing the draw-down procedure. One or more recirculation pumps are located in the chamber.

Automated valves to open and close the vacuum-water ports are located on the central column in the influent-effluent chamber. Another pump and automated valve system is situated at the tank perimeter to provide the partial vacuum for algal slurry removal and to pump influent and effluent in the dual-purpose lines. A pump station at the waist can carry out these functions for both nodes and also to pump influent to the center island. Chemical additives may be introduced at the pump 252 location.

Figure 41:
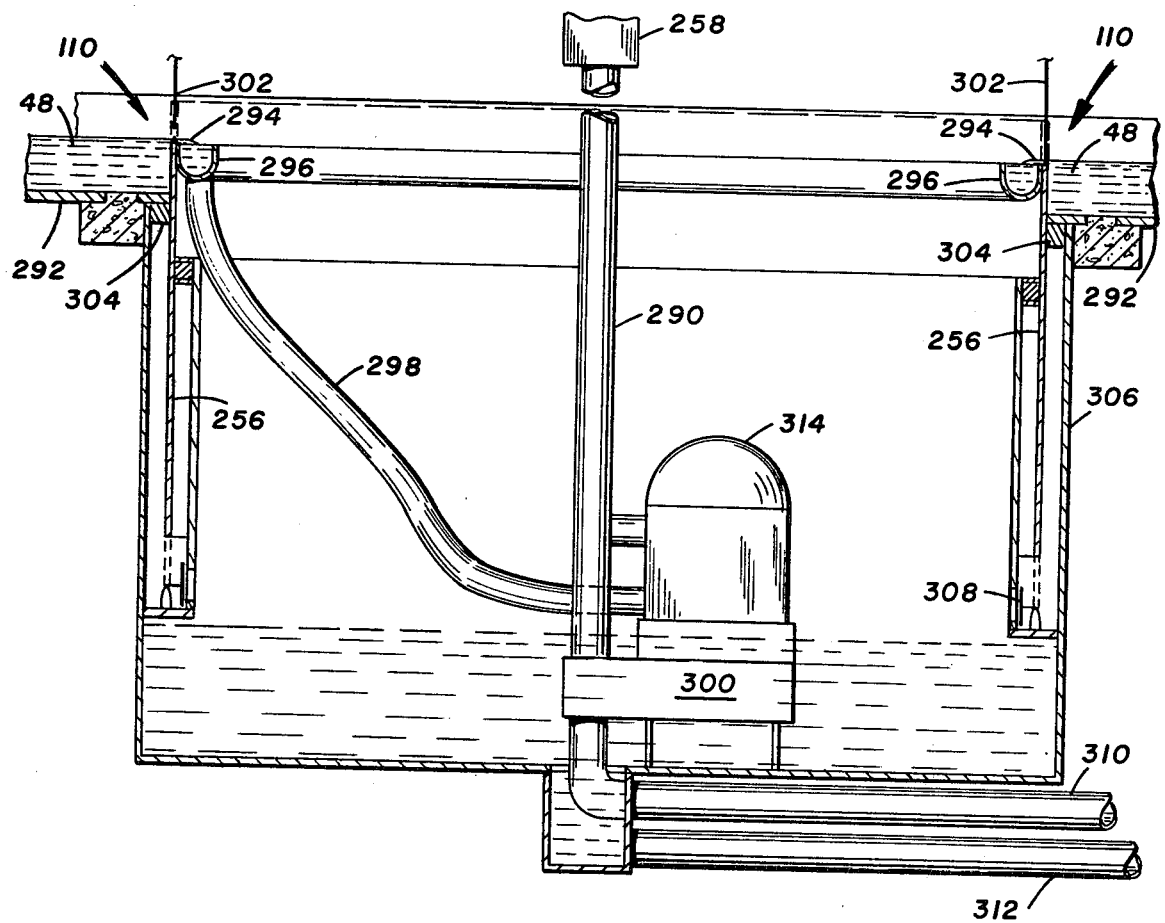
FIG. 41 is a cross sectional view of the weir of the third embodiment of an A-6 Tank.

The circular weir 256 of the control tank is made of transparent or translucent material for light transmission into the culture liquid. It is raised and lowered by a system of cables 302 from the weir 256 via pulleys and booms (not shown) to an electric motor and reels (not shown) on the central column 290. The motor is gravity-assisted when the weir 256 is lowered by the combined weight of the descending weir and the decanted water in the cup, thus assuring a smooth and stabilizing descent. During slow refill, influent is through the center island and the weirs are raised by the electric motors to operating tank-water depth, unburdened by water in the decanter cups. During fast refill, when the control units are also utilized, the electric motors must lift the weirs plus the water in the cups that is decanted back into the A-6 tank 110. Weir 256 details (above) are shown in FIG. 41.

To minimize leakage at the interface of the tank floor 292 and the weir, close fitting circular sectional flanges and gaskets 304 are installed around the weir 256 at the A-6 tank floor. A leakage container 306, with packing boxes enclosing the weir 256 below the tank floor 292, contains any leakage of algae-laden water at the aforementioned interface and prevents such leakage from mixing with decanted algae-free final effluent during draw-down. A pressure valve 308 in the leakage container bleeds off excess water. When draw-down is completed and the weir 256 is completely down, a tripping device opens the valve to empty the leakage from the container into the sump. These details of the weir 256 are shown in FIG. 41.

Primary concentration is accomplished in the third embodiment of the A-6 tank 110 by sedimentation with or without coagulants, then draw-down and vacuum sweep.

It is to be noted that if space conservation is required, the A-6 tanks 110 may be clustered by fitting the wide nodal areas into the narrow waist area of an adjoining tank. Thus, six or more "eight shaped" A-6 tanks can be nested or jig-sawed in a close formation to conserve surface area of the layout.

Bypass channels 266 speed up the circulation of the culture liquid and getting it into the main stream for quicker passage through the previous nodal system. Vertical waterwheels or mixer impellers 268, electric- or wind-powered, in the bypass channels 266 increase the flow velocity in the channels 266.

Incoming influent 250 entering the central area at the waist is pumped in at the central island by the pump 244. This influent is disbursed through the array of nozzles 270 into the circulating stream of culture liquid.

Figure 38:
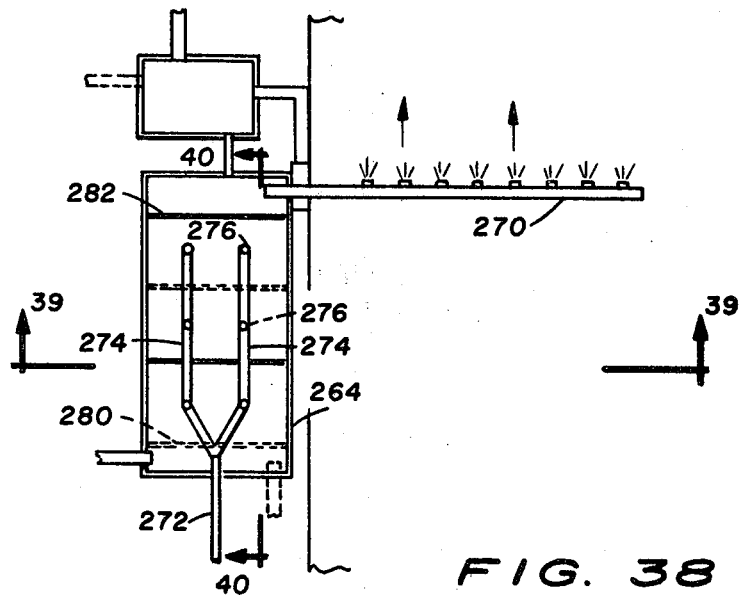
FIG. 38 is a plan view of a gas diffusion system.
Figure 39:
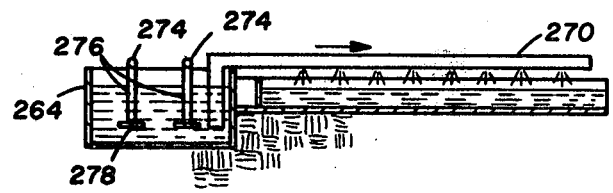
FIG. 39 is a cross sectional view on line 39—39 of FIG. 38.
Figure 40:
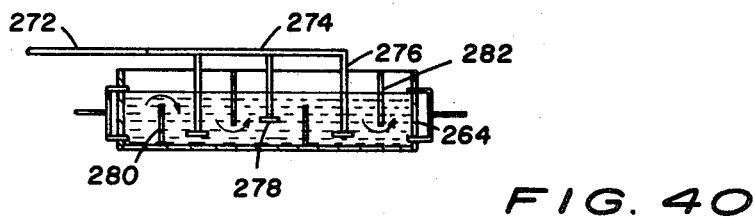
FIG. 40 is a cross sectional view on line 40—40 of FIG. 38.

As to the matter of $CO_2$ gas diffusion into the culture liquid influent of the A-6 tanks 110 (all three embodiments), FIG. 38 shows a plan view of the gas diffusion system. Diffusion of $CO_2$ mixed with air into the culture liquid has been discussed previously, but has not been described in detail. Gas enters the gas diffusion chambers 264 at the gas inlet 272. The gas flows through the horizontal piping system 274 and then down the vertical legs 276 to the diffusion heads 278 where the gas is diffused counter-current into the culture liquid. The diffusion heads 278 are equipped with multiple, open-valve disc-diffusers, not shown, which seal openings when the gas is shut off.

The culture liquid passing through the gas diffusion chamber 264 passes over and under a series of baffles to minimize short-circuiting and to assure complete mixing. The culture liquid passes over the lower baffles 280 and under the upper baffles 282 to provide a complete mix of the $CO_2$-in-air gas and culture liquid. The pressurized air-$CO_2$ gas mixture in the gas space at the top of the gas diffusion tank provides additional gas-water transfer efficiency in two ways: at the water surface; and by mechanical means to force the gas into the liquid through gas recirculation pipes equipped with check valve to prevent water backflow. Valves to relieve excess pressures and to remove diluted $CO_2$-in-air mixtures in the gas space are not shown.

A typical location in the center island for a gas diffusion chamber 264 is shown in the third embodiment of A-6 tank 110 (FIG. 37) as gas distribution chamber 284. The gas diffusion chamber 264 is enclosed and gas-tight. The gas diffusion chamber 264 provides a means for diffusing the gas directly into the liquid culture. The gas treated culture liquid is then put back into the flowing steam by distributing it through the array of nozzles 270.

Turning now to the gas diffusion into the effluent. In the first and second embodiment of the A-6 tank 110 particularly, and in third embodiment under certain circumstances, when the effluent is piped from one A-6 tank 110 into another A-6 tank 110 in a series set up, $CO_2$ gas is diffused into the effluent in preparation for the culture liquid processing in the latter A-6 tank 110. The effluent gas diffusion chamber is, of course, at the "outlet" of the A-6 tank 110 concerned. The system is similar to the gas diffusion into the influent liquid, except that after the gas diffusion has been made, the liquid is directed to the next A-6 tank 110 instead of discharging it through an array of nozzles into the culture liquid of the originating A-6 tank 110. The effluent gas diffusion chambers are enclosed, have baffles, a piping system for the gas, vertical legs of the piping system leading into the gas diffusion chamber, and gas diffusion heads down in the liquid. All essentially the same as for the gas diffusion for the influent liquid.

Another means of producing the algae growth, either in conjunction with the A-Tank system as described or as a substitution for the third embodiment of the A-6 tank, is to use a circular A-type tank embodying the features of just one of the two nodes of the third embodiment of the A-6 tank, the circular-type A-tank may be referred to as an A-7 tank. The A-7 tank has not been illustrated in the drawings.

In regard to the plastics tube channel 148 and the special tube-like transition piece, the transition piece is a hard plastics. The transition piece is equipped with a gas relief valve which is vented to the atmosphere. Special configuration of the tube-like transition pieces are used to connect sections of the main tube channel 148 together, and to connect the main tube channel 148 to the inlet and outlet lips of the control tank 124. In addition to the plastics tube channels being transparent, the transition-piece connectors and the control tank covers are also transparent.

The plastics tube channels 148 may be set in the cradle 150 and held in place by the liquid carried in the tube. However, it is to be understood that tie-down means may be used to secure the plastics tube channels 148 in place. Such tie-down means may be placed across the top of the tube transition pieces or attached to ears or lugs on the sides of the tube transition pieces.

It is to be understood that where $CO_2$ gas generated by the system is insufficient, supplemental $CO_2$ gas from on-site bulk tanks may be used.

A disinfection system is included in the water disposal means to disinfect the reclaimable water from the controlled natural purification system after the algae is removed.

The bacteriological process in the controlled natural purification process is described hereinafter.

Biochemical oxygen demand is reduced in the anaerobic filters by acid-forming and methane-forming bacteria to produce methane and carbon dioxide in an anoxic environment.

The biochemical oxygen demand is further reduced in the aeration tanks 70 and 72 by the facultative saprophytic bacteria which feed on the degradable organic matter in the presence of dissolved oxygen.

Reduction of organic matter exerting biochemical oxygen demand that is carried over into the A-tank complex is continued by the saprophytic bacteria in a symbiotic oxygen-carbon dioxide exchange with the algae in the photosynthetic process.

Nitrification is accomplished in the aeration tanks 70 and 72 by a special group of facultative autotrophic bacteria. These microbes derive energy by oxidizing ammonia to nitrite and thence to nitrate. Carbon for synthesis of cellular material is derived from carbon dioxide produced in the oxidation of the organic material. One half of the nitrifying bacteria are returned to the aeration tanks 70 and 72 via the recirculation tanks 74, 76, 78 and 80. Since the nitrifying bacteria are facultative, they are expected to survive anaerobic treatment in the filters 86, 88, 90, and 92 if such treatment is required.

Denitrification takes place in an anoxic environment. Anaerobic denitrification filters 86, 88, 90 and 92 where facultative heterotrophic organisms convert the nitrates to nitrogen gas by utilizing nitrate as an oxidizing agent in the absence of dissolved oxygen. A carbon source provided by the remaining organic matter and dissolved carbon dioxide provides food and energy to the denitrifiers.

Where the system is used for algae farming there will be no excess nutrients such as nitrogen and phosphorus. Therefore, the removal processes (i.e., denitrification filters in the case of nitrogen removal and precipitation in the case of phosphorus removal will not be required.

The A-Tank complex for algae culture and harvest may be used for culturing algae in mediums other than organic wastewater. One such other medium would be salt water. Thus, the system of an A-Tank complex may be used in the culture of algae for the production of glycerol, fats, and other commercially valuable products.

In both the anaerobic filters and the anaerobic denitrification filters they have a rock filter medium in the up-flow at the baffle area to trap suspended solids for fermentation and retention longer than normal flow-through period.

Regarding the connection of A-6 tanks 100 in series and in parallel (FIGS. 35 and 36) the arrangement is accomplished as hereinafter described.

In FIG. 35, influent 226 to the system is processed in the B-Tank Complex and discharged as culture liquid 228. Part of the culture liquid 228 is stored in tanks 222 and 224 as hereinbefore described, and part of piped by piping 230 to the A-1 tank 100 over the top of the B-Tank Complex. Culture liquid from the A-1 Tank 100 is piped 232 to the A-2 through A-5 tanks (not shown) and the subsequently to the first A-6 tank 110 in the series. Thereafter the series connection is accomplished by piping 236. The discharge from each A-6 tank 110 is through pipine 238 to the algae harvesting complex 240 (concentration, dewatering, and drying). Gas diffusion is accommplished to all A-6 tanks 110 through piping 234.

In a like manner, the same numbered elements apply to the series-parallel arrangement in FIG. 36, except that the piping 232 is directed first to two of the illustrated A-6-110 tanks to place them in parallel, but then an additional tank is connected in series, to each of the tanks in parallel, by piping 236 as shown.

It is to be noted that advanced wastewater requires the removal of nutrients, nitrogen, and phosphorus. When the removal of nitrate nitrogen over and above algal photosynthetic needs is not required, the following steps in the controlled natural purification process are eliminated: denitrification in the denitrification filters, and reaeration in the recirculation tanks to discharge nitrogen gas in solution from the recirculating water in the B-Tank Complex. Excess phosphorous, however, is usually removed in the harvesting process.

As referred to hereinbefore, phosphorus in excess of that removed by algae in metabolic uptake, is removed by precipitation. This precipitation is accomplished at algae harvest time by inducing a high pH by reduction of $CO_2$ in solution. This is done by photosynthesis and controlled $CO_2$-air diffusion. This step in the controlled natural purification process also enhances the recovery of the algae by sedimentation. The elevated pH (in the range of 9.0 to 10.0) causes the removal of phosphorus from solution by the rapid formation and precipitation of insoluble phosphates without the use or need of auxiliary chemicals. The settleability of the algae is increased by the resulting adsorption and coagulation.

As can be readily understood from the foregoing description of the invention, the present structure can be configured in different modes to provide the ability to treat wastewater and convert certain elements to a protein substance and to recover that protein substance.

Accordingly, modifications and variations to which the invention is susceptible may be practiced without departing from the scope and intent of the appended claims.

What is claimed is:

1. A method for controlling the natural purification of settled organic wastewater to provide an advanced wastewater treatment to produce a conversion to microalgae and recovery of same, comprising, first processing the settled organic wastewater by a treatment procedure without a light source, second processing the partially treated wastewater from the first process by a treatment procedure with a light source, causing aeration and turbulence within the wastewater during both the first and second treatment procedures, causing biochemical oxygen demand reduction, nitrification and denitrification, and nitrate-nitrogen removal during the first treatment procedure, and causing biochemical oxygen demand reduction, phosphate-phosphorous removal during the second treatment procedure, and thereafter harvesting microalgal and discharging reclaimable water.

2. A controlled natural purification system for advanced wastewater treatment and microalgae conversion and recovery, comprising:

a first processing tank system, said first processing tank system being fully enclosed and operating without any exposure to daylight;

a second processing tank system, said second processing tank system being exposed to daylight, said second processing tank system being connected to said first tank procession system;

a microalgal harvesting system, said microalgal harvesting system being connected to said second processing tank system;

and a sewerage disposal sedimentation system, said first processing tank system being installed after said sewerage disposal sedimentation system, said first processing tank system receiving settled organic wastewater therefrom as influent for processing, said first processing tank system consists of:

at least one equalization tank, said equalization tank being installed within said first processing tank system, said equilization tank receiving said settled organic wastewater for initial storage and equalization of temperature and flow rate;

at least one anaerobic filter means, said anaerobic filter means being connected to said equalization tank and receiving influent therefrom;

at least one aerobic treatment tank, said aerobic treatement tank being connected to said anaerobic filter means and receiving influent therefrom;

at least two recirculation tanks for each said aerobic treatment tank, said recirculation tanks being connected to said aerobic treatment tank and receiving influent therefrom for recirculation and later discharge back into said aerobic treatment tank;

at least one denitrification means for each said recirculation tank, said denitrification means being anaerobic denitrification filters, each said denitrification means being connected to said aerobic treatment tank and then further connected to one of said recirculation tanks, said denitrification means receiving said influent from said aerobic tank to stabilize excessive nitrogen in solution as needed during certain seasonal operations and then discharging said influent into said recirculation tank for removal by reaeration;

a first carbon dioxide collecting means, said carbon dioxide collecting means being connected to said first tank system;

a first sludge removal means, said first sludge removal means being installed in said first tank system;

a first methane gas collection means, said first methane gas collection means being connected to said anaerboic filter means;

a first plurality of aerators, said first plurality of aerators being installed in said aerobic treatment tank, said first plurality of aerators aerating air through said influent and causing turbulence therein as it passes through said aerobic treatment tank;

a second plurality of aerators, said second plurality of aerators being installed in said recirculation tanks, said second plurality of aerators aerating air through said influent as it passes through said recirculation tanks;

a baffle means, said baffle means being installed in said recirculation tanks to provide a directional flow control and turbulence in said influent being recirculated; and a first piping system, said first piping system interconnecting all elements of said first processing tank system as herein provided and connecting said first processing tank system to said second processing tank system to transfer said influent after processing in said first processing tank system.

3. The controlled natural purification system as recited in claim 2, wherein said second processing tank system consists of:

a first tank means, said first tank means being located on top of said first processing tank system and thereby forming the enclosing cover for said first processing tank system, said first tank means receiving said processed influent from said first processing tank system for further treatment;

a plurality of second tank means, said plurality of second tank means being connected to said first tank means, said plurality of second tank means receiving treated influent from said first tank means for further treatment, said plurality of second tank means being connected in sequence, said plurality of second tank means connected in sequence being sequentially located on a descending incline;

at least one third tank means, said third tank means being connected to said plurality of second tank means, said third tank means being located more or less on a level horizontal plane, said third tank means receiving treated influent from said second tank means for final treatment;

a means of creating aeration and turbulence in said second processing tank system, said means of creating aeration and turbulence being installed in the path of said influent being treated;

a second sludge removal means, said second sludge removal means being installed in said second tank system;

a carbon dioxide distribution means, said carbon dioxide distribution means being installed in second processing tank system and connected to said first carbon dioxide collection means and receiving carbon dioxide therefrom for distribution into said influent being treated together with supplemental carbon dioxide from an on-site bulk system and from other in-process means, in said second processing tank system; and a second piping system, said second piping system interconnecting all elements of said second processing tank system as herein provided and connecting said second processing tank system to said microalgal harvesting system.

4. The controlled natural purification system as recited in claim 3, wherein said microalgae harvesting system consists of:

an algae slurry collection means, said algae slurry collection means being installed in and connected to said second processing tank system;

a dewatering means to dewater harvested algae, said dewatering means connected to said algae slurry collection means;

a drying means, said drying means connected to said dewatering means to dry dewatered algae and produce an algae meal;

a water disposal means, said water disposal means connected to said second processing tank system and to said dewatering means to receive water for disposal, said water disposal means having a water disinfection system to disinfect said water before final disposal as reclaimable water; and a piping means, said piping means interconnecting all elements of said microalgae harvesting system as herein provided.

5. The controlled natural purification system as recited in claim 3, wherein said first tank means consists of:

a plurality of pairs of channels, said plurality of pairs of channels being arranged side by side, a first channel of each pair of channels being so elevated so as to cause liquid therein to flow in a first direction, the other second channel of each pair of channels being so elevated so as to cause liquid therein to flow in a second direction opposite to that in said first channel;

a plurality of control tanks, one of said plurality of said control tanks being located at each end of each said pair of channels, each said control tank connecting the end of one channel of one pair of channels to the adjacent channel of the next succeeding pair of channels, said control tanks providing the means for transmitting and transferring said liquid sequentially from one pair of channels to the next adjacent pair of channels, said control tanks having a portion of said algae harvesting system installed therein.

6. The controlled natural purification system as recited in claim 5, wherein said channels are open and trench-like.

7. The controlled natural purification system as recited in claim 5, wherein said channels are flexible tube-like means, a cradle-like means, said flexible tube-like means being transparent and held in position by said cradle-like means, said cradle-like means sloping in the direction of flow of said channel, and additionally, a transparent transition cover at each said control tank, a connection means, said tube-like means being connected to said transparent transition covers on said control tanks and connected to each other by said connection means.

8. The controlled natural purification system as recited in claim 7, wherein said transfer of said liquid through said control tanks to succeeding channels of said pairs of channels produces turbulence, and a plurality of rod-like means under each said tube-like channel means to cause additional turbulence in said liquid.

9. The controlled natural purification system as recited in claim 7, wherein each said second tank means structure is a reproduction of said first tank means and located on said descending incline.

10. The controlled natural purification system as recited in claim 5, and additionally an extension tank means to said control tanks, and a controlled immersed artifical lighting system in said extension tank means.

11. The controlled natural purification system as recited in claim 10, wherein said artificial lighting system is composed of a plurality of light clusters, each said light cluster consisting of:
a top frame means;
a bottom frame means, a centering node means, said bottom frame means having the centering node means centrally located on the exterior thereof, said bottom frame means being spaced apart from said top frame means;
a transparent hollow cylindrical watertight enclosure means, said enclosure means being set between and attached to said top frame means and said bottom frame means;
a plurality of electrical lamp means set between and electrically connected to said top frame means and said bottom frame means and being inside said enclosure means;
a light reflector means, said light reflector means having a plurality of reflector surfaces to individually match said plurality of lamp means; and
a centering base means, said centering base having a centrally located depression therein to mate with and receive said centering node means of said bottom frame means, said centering base means being affixed to the underwater bottom inside of said extension tank means.

12. The controlled natural purification system as recited in claim 3, wherein said third tank means is substantially figure eight shaped having a nodal configuration at each end of said figure eight shape, circularly moving piping means in said third tank means, said circularly moving piping means disbursing said liquid, from said second tank means, below the liquid level therein, said disbursion of liquid causing turbulence in said liquid in said third tank means, said circularly moving piping means having a capability for connection to a vacuum system as part or said algae harvesting system.

13. The controlled natural purification system as recited in claim 12, and additionally a circular weir means centered around a center column of said circularly moving piping means, said circular weir means being a control mechanism, a cable means for raising and lowering said circular weir means, a circular decanter cup-like means in said circular weir means around the inside periphery thereof, treated liquid overflowing said circular weir means being captured by said circular decanter cup-like means and conducted through flexible pipe means to pump means for distribution to said circularly moving piping means through a rotating manifold means.

14. The controlled natural purification system as recited in claim 13, and additionally, a gasket and flange means between exterior surface of said circular weir means and the surrounding floor of said third tank means, said gasket and flange means incorporating a leakage container and disposal means.

15. The controlled natural purification system as recited in claim 2, and additionally a sludge processing system, said sludge processing system being connected to said sedimentation system from which said sludge processing system receives sludge for procesing, said sludge processing system having a second methane gas collection means, said first and second methane gas collection means supplying methane gas for sludge processing system and algae drying, said sludge processing system having a second carbon dioxide collecting means, said second carbon dioxide collecting means supplying supplemental carbon dioxide to said second processing tank system, said sludge processing system producing a supernatant liquor which is transferred to and mixed with said influent being supplied to said first tank processing system.

16. The controlled natural purification system as recited in claim 3, wherein said third tank means is substantially figure eight shaped, having a nodal configuration at each end of said figure eight shape, each said nodal configuration having vanes therein to direct the flow of said liquid, an impeller means in said third tank, said impeller means providing turbulence in said liquid, piping means in said third tank means to disburse said liquid, from said second tank means, to the liquid surface area of said third tank means, said third tank means having a portion of said algae harvesting system installed therein.

17. Apparatus for controlling the nautral purification of settled organic wastewater to provide an advanced wastewater treatment to produce conversion to microalgae and recovery thereof, comprising, a first means for processing settled organic wastewater by a first treatment procedure without a light source, a second means for processing the partially treated wastewater from said first means by a second treatment procedure with a light source, means for causing aeration within the wastewater in said first and second means during both the first and second treatment procedures, means for causing turbulence within the wastewater in said first and second means during both the first and second treatment procedures, means for causing biochemical oxygen demand reduction in the wastewater during the first treatment procedure, means for causing nitrification in the wastewater during the first treatment procedure, means for causing denitrification in the wastewater during the first treatment procedure, and means for causing nitrate-nitrogen removal in the wastewater during the first treatment procedure, means for causing biochemical oxygen demand reduction in the wastewater during the second treatment procedure, means for causing phosphate-phosphorous removal from the wastewater during the second treatment procedure, means for harvesting the microalgae from the wastewater, and means for discharging reclaimable waste water.

* * * * *

UNITED STATES PATENT AND TRADEMARK OFFICE
CERTIFICATE OF CORRECTION

PATENT NO. : 4,267,038
DATED : May 12, 1981
INVENTOR(S) : Worthington J. Thompson It is certified that error appears in the above—identified patent and that said Letters Patent is hereby corrected as shown below:

In the Specification:

Col. 7, line 3, after "and" insert -- aerobic --.

Col. 8, line 29, delete "excesive" and insert -- excessive --.

Col. 13, line 25, delete "a" and insert -- at --.

Col. 29, line 23, delete "pipine" and insert -- piping --.

In the Claims:

Col. 31, line 3, delete "anaerboic" and insert -- anaerobic --.

Col. 34, line 31, delete "nautral" and insert -- natural --.

Signed and Sealed this

Eighteenth Day of August 1981

[SEAL]

Attest:

GERALD J. MOSSINGHOFF

Attesting Officer    Commissioner of Patents and Trademarks